United States Patent [19]

Iijima et al.

[11] Patent Number: 4,612,317
[45] Date of Patent: Sep. 16, 1986

[54] TETRAHYDRO-β-CARBOLINE DITHIOIC ACID DERIVATIVES AND TREATMENT OF LIVER DISEASES

[75] Inventors: Ikuo Iijima, Urawa; Yutaka Saiga, Ageo; Toshikazu Miyagishima, Wako; Yuzo Matsuoka, Tondabayashi; Mamoru Matsumoto, Nara, all of Japan

[73] Assignee: Tanabe Seiyaku Co., Ltd., Osaka, Japan

[21] Appl. No.: 611,965

[22] Filed: May 18, 1984

[30] Foreign Application Priority Data

Jun. 4, 1983 [GB] United Kingdom ............... 8315403

[51] Int. Cl.$^4$ .................. A61K 31/435; C07D 471/04
[52] U.S. Cl. ........................................ 514/292; 546/85; 546/87
[58] Field of Search ............... 546/85, 87; 514/292

[56] References Cited

U.S. PATENT DOCUMENTS

2,187,719  1/1940  Williams .................... 546/85

FOREIGN PATENT DOCUMENTS

| 668301 | 8/1963 | Canada | 546/85 |
|---|---|---|---|
| 20923 | 2/1961 | Fed. Rep. of Germany | 546/85 |
| 1837M | 4/1964 | France | 546/85 |
| 0031097 | 3/1977 | Japan | 546/85 |

OTHER PUBLICATIONS

Zimmerman, H. J., "Hepatotoxicity-The Adverse Effects of Drugs and Other Chemicals on the Liver", Appleton-Century-Crofts, New York (1978).

*Primary Examiner*—Henry R. Jiles
*Assistant Examiner*—Dale A. Bjorkman
*Attorney, Agent, or Firm*—Birch, Stewart, Kolasch & Birch

[57] ABSTRACT

Tetrahydro-β-carboline derivatives of the formula:

(I)

wherein $R^1$ is hydrogen atom, a lower alkyl group, a cycloalkyl group, phenyl group or a hydroxy-substituted lower alkyl group, $R^2$ is hydrogen atom, an alkyl group, or a group of the formula: $-(CH_2)_mY$, Y is thienyl or a substituted or unsubstituted phenyl group, and m and n are an integer of 1 or 2, which have excellent alleviating, curing and preventing hepatic damages and are useful as a therapeutic or prophylactic agent for hepatic diseases, and a process for the preparation of said compounds.

37 Claims, No Drawings

TETRAHYDRO-β-CARBOLINE DITHIOIC ACID DERIVATIVES AND TREATMENT OF LIVER DISEASES

The present invention relates to novel tetrahydro-β-carboline derivatives of the formula:

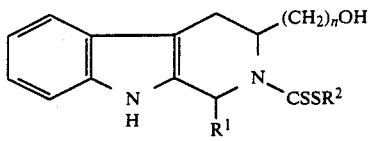

wherein $R^1$ is hydrogen atom, a lower alkyl group, a cycloalkyl group, a phenyl group or a hydroxy-substituted lower alkyl group, $R^2$ is hydrogen atom, an alkyl group, or a group of the formula: —$(CH_2)_mY$, Y is thienyl group or a substituted or unsubstituted phenyl group and each one of m and n is an integer of 1 or 2, and a process for the preparation thereof. This invention includes a pharmaceutically acceptable salt of the compound (I) wherein $R^2$ is hydrogen atom or a group of the formula: —$(CH_2)_mY$ and Y is an amino-phenyl group.

The liver is an organ having various functions such as detoxication, carbohydrate metabolism, lipid metabolism, protein metabolism, production and secretion of bile, production of blood coagulation factors, control of hormones, regeneration of liver cells, storage of living body-constituting elements (e.g. fats, glycogen, proteins, vitamins), and the like. These functions are acutely or chronically disordered by various causes such as virus, drugs, poisons, alcohols, insufficient nutrition, vascular dysfunction of the liver, obstruction of the bile duct, or the like. These liver function disorders appear clinically in the form of a viral hepatitis, drug-induced hepatopathy, alcoholic hepatitis, congestive hepatitis, hepatic disease caused by bile-congestion, fatty liver, jaundice, and finally hepatocirrhosis, or the like.

The novel tetrahydro-β-carboline derivatives of the formula (I) and a pharmaceutically acceptable salt thereof are useful as a therapeutic or prophylactic agent for hepatic diseases because they exhibit excellent activities for alleviating or curing hepatic damages and also for protecting the liver from hepatic damages.

The tetrahydro-β-carboline derivatives of the present invention include compounds of the formula (I) wherein $R^1$ is hydrogen atom, a lower alkyl group having 1 to 4 carbon atoms, such as methyl, ethyl, propyl, or butyl group, a cycloalkyl group having 5 to 6 carbon atoms, such as cyclopentyl or cyclohexyl group, phenyl group or a hydroxy-lower alkyl group having 1 to 4 carbon atoms, such as hydroxymethyl, hydroxyethyl, hydroxypropyl, or hydroxybutyl group; $R^2$ is hydrogen atom, an alkyl group having 1 to 10 carbon atoms, such as methyl, ethyl, propyl, butyl, pentyl, hexyl, heptyl, octyl, nonyl or decyl group, or a group of the formula: —$(CH_2)_mY$ wherein Y is thienyl, phenyl or a phenyl substituted by a substituent selected from the group consisting of a halogen atom (e.g. chlorine, bromine, iodine or fluorine), formylamino, amino, nitro, a lower alkyl group having 1 to 4 carbon atoms (e.g. methyl, ethyl, propyl, or butyl), and a lower alkoxy group having 1 to 4 carbon atoms (e.g. methoxy, ethoxy, propoxy, or butoxy); m and n are each an integer of 1 or 2.

Preferred compounds are compounds of the formula (I) wherein $R^1$ is hydrogen atom, methyl, ethyl, propyl, butyl, hydroxymethyl, cyclohexyl, or phenyl group; $R^2$ is hydrogen atom, methyl, ethyl, propyl, butyl, hexyl, decyl, benzyl, 2-thenyl (=thienylmethyl), phenylethyl, 4-chlorobenzyl, 4-(N-formylamino)benzyl, 4-aminobenzyl, 4-nitrobenzyl, 4-methylbenzyl, or 4-methoxybenzyl group; and n is an integer of 1 or 2. More preferred compounds are compounds of the formula (I) wherein $R^1$ is hydrogen atom, methyl, ethyl, or hydroxymethyl group; $R^2$ is hydrogen atom, methyl, ethyl, propyl, butyl, benzyl, 4-chlorobenzyl, 2-thenyl, or 4-methoxybenzyl group; and n is an integer of 1. Particularly preferred compounds are compounds of the formula (I) wherein $R^1$ is hydrogen atom or methyl group; $R^2$ is hydrogen atom, methyl, ethyl, propyl, butyl, benzyl, 4-chlorobenzyl, 2-thenyl, or 4-methoxybenzyl group; and n is an integer of 1. Still further particularly preferred compounds are compounds of the formula (I) wherein $R^1$ is hydrogen atom or methyl group; $R^2$ is hydrogen atom, methyl, or ethyl group; and n is an integer of 1.

Other preferred compounds are compounds of the formula (I) wherein $R^1$ is hydrogen atom; $R^2$ is methyl or 4-chlorobenzyl group; and n is an integer of 2, and more preferred compounds are compounds of the formula (I) wherein $R^1$ is hydrogen atom; $R^2$ is methyl group; and n is an integer of 2.

The compounds of the formula (I) wherein $R^2$ is hydrogen atom or a group of the formula: —$(CH_2)_mY$ (wherein Y is an amino-phenyl group) may be used in the form of a pharmaceutically acceptable salt. When $R^2$ is hydrogen atom, suitable examples of the salt are a salt of an alkali metal such as sodium or potassium, and a salt of an organic amine, such as trimethylamine, triethylamine, N-methylmorpholine, or dicyclohexylamine. When $R^2$ is a group of the formula: —$(CH_2)_mY$, suitable examples of the salt are a mineral acid salt such as hydrochloride, sulfate, an aromatic sulfonate such as benzenesulfonate, toluenesulfonate, and an alkylsulfonate such as methanesulfonate, ethanesulfonate.

The compounds of the formula (I) wherein $R^1$ is a hydrogen atom include two optical isomers and a racemic mixture. Besides, the compounds of the formula (I) wherein $R^1$ is a lower alkyl group, a cycloalkyl group, a hydroxy-lower alkyl group, or phenyl group include two stereoisomers (i.e. cis- and trans-isomers), and each stereoisomer includes further two optical isomers and a racemic mixture. The present invention includes within its scope these isomers and a mixture thereof.

According to the present invention, the compound of the formula:

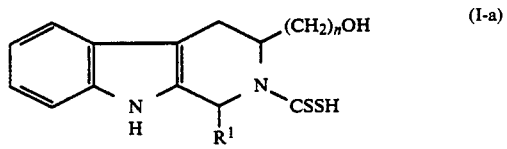

wherein $R^1$ and n are as defined above, or a pharmaceutically acceptable salt thereof can be prepared by reacting a compound of the formula:

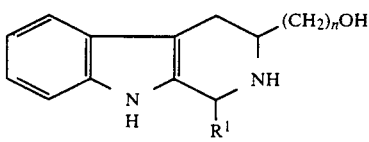

wherein R¹ and n are as defined above with carbon disulfide, optionally followed by converting the resulting compound into a pharmaceutically acceptable salt thereof.

Alternatively, a compound of the formula:

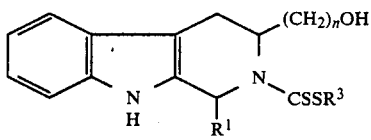

wherein $R^3$ is an alkyl group or a group of the formula: —$(CH_2)_mY$, and $R^1$, Y, m and n are as defined above, can be prepared by reacting a compound of the formula (II) with carbon disulfide and a compound of the formula:

$$R^3-X \qquad (III)$$

wherein $R^3$ is as defined above, and X is a halogen atom.

Alternatively, a compound of the formula (I) wherein $R^2$ is a group of the formula: —$(CH_2)_mY$ and Y is an amino-phenyl group, or a pharmaceutically acceptable salt thereof can be prepared by removing a protecting group from a compound of the formula (I) wherein $R^2$ is a group of the formula: —$(CH_2)_mY$ and Y is a protected amino-phenyl, and optionally followed by converting the product into a pharmaceutically acceptable salt thereof.

These processes are explained in more detail below.

The reaction of the compound (II) with carbon disulfide is carried out in a solvent in the presence of a base. The base includes inorganic bases such as, for example, alkali metal hydroxides (e.g. sodium hydroxide, potassium hydroxide), alkali metal carbonates (e.g. sodium carbonate, potassium carbonate), and organic amines (e.g. trimethylamine, triethylamine, N-methylmorpholine, dicyclohexylamine). Suitable examples of the solvent are water, methanol, ethanol, dimethylsulfoxide, tetrahydrofuran, dioxane, dimethylformamide, or a mixture thereof. The carbon disulfide and the base are usually used in an amount of 1 to 10 equivalents, preferably 1 to 5 equivalents, per mole of the compound (II). The reaction temperature is in the range of 0° to 50° C., preferably 10° to 30° C. The compound (I-a) obtained by the reaction is preferably recovered from the reaction mixture in the form of a salt thereof.

The reaction of the starting compound (II), carbon disulfide and the compound (III) is carried out in a solvent and in the presence of a base. The base includes inorganic bases, for example, alkali metal hydroxide such as sodium hydroxide, potassium hydroxide or lithium hydroxide, alkali metal carbonate such as sodium carbonate or potassium carbonate, and organic amines such as trimethylamine, triethylamine, N-methylmorpholine or dicyclohexylamine. Suitable examples of the solvent are water, methanol, ethanol, dimethylsulfoxide, tetrahydrofuran, dioxane, dimethylformamide, or a mixture thereof. The reaction is preferably carried out by firstly reacting the compound (II) and carbon disulfide in a solvent in the presence of a base and then adding the compound (III) to the reaction mixture. The carbon disulfide, the base and the compound (III) are each used in an amount of 1 to 10 equivalents, preferably 1 to 5 equivalents, per mole of the compound (II). The reaction is carried out at a temperature of 0° to 50° C., preferably 10° to 30° C.

When the compound obtained in the above-mentioned process is a compound of the formula (I) wherein $R^2$ is a group of the formula —$(CH_2)_mY$ and Y is a protected aminophenyl group, the removal of the protecting group is carried out in conventional manner. For example, if the protecting group is an acyl group such as formyl, acetyl, it is removed by treating the protected compound with a mineral acid (e.g. hydrochloric acid, hydrobromic acid, sulfuric acid). Besides, if the protecting group is benzyloxycarbonyl, it is removed by catalytically reducing the protected compound in the presence of a catalyst (e.g. Pd/C, Pt). Any other groups which have been usually used to protect amino group in peptide synthesis may be used to protect said amino-phenyl group, and these groups may be readily removed therefrom by per se known methods.

The above reactions can proceed without racemization, and hence, when an optical active compound (II) is used, the desired compounds (I-a) and (I-b) are also obtained in an optically active form.

The starting compounds (II) can be prepared, for example, by the processes of the following reaction schemes:

Process A

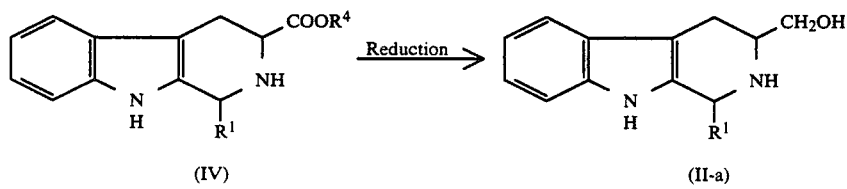

Process B

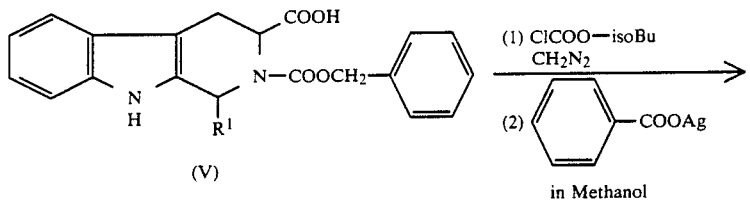

(V)

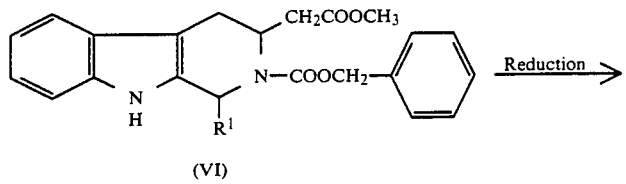

(VI)

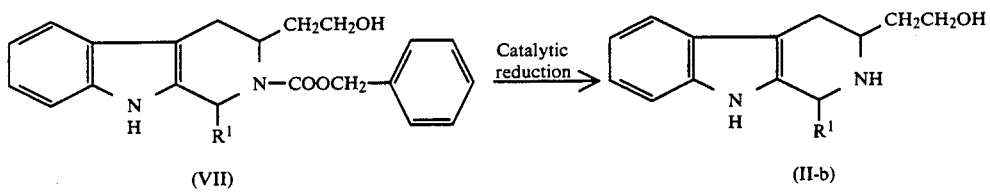

wherein R⁴ is an ester residue, and $R^1$ is as defined above.

According to Process A, the compound (II-a), i.e. the compound (II) wherein n is 1, can be prepared by reducing the compound (IV) with a metal hydride (e.g. lithium aluminum hydride, sodium borohydride) either under cooling (e.g. at about 0° C.) or under refluxing in a solvent (e.g. tetrahydrofuran, dimethoxyethane, dioxane, water, ethanol, aqueous ethanol).

According to Process B, the compound (II-b), i.e. the compound (II) wherein n is 2, can be prepared by reacting the compound (V) with isobutyl chloroformate and diazomethane under cooling in a solvent (e.g. tetrahydrofuran, dioxane, dimethylformamide, dimethylacetamide), treating thus-obtained compound with silver benzoate at room temperature in methanol, reducing the resulting compound (VI) with a metal hydride (e.g. sodium borohydride, lithium aluminum hydride) under cooling in a solvent (e.g. ethanol, tetrahydrofuran, water, dioxane, aqueous ethanol), and further catalytically reducing the resulting compound (VII) at room temperature in a solvent (e.g. methanol, ethanol, ethyl acetate, tetrahydrofuran, aqueous ethanol, aqueous methanol) in the presence of a catalyst (e.g. Pd-C, Pt) under atomospheric pressure.

When the starting compound (IV) or (V) in the above Processes A and B is used in an optically active form, there can be obtained the corresponding optically active compound (II-a) or (II-b).

The starting compound (IV) used in the above Process A may be prepared by a process as shown in the following reaction scheme [cf. J. Med. Chem., 16, 418 (1973); Yakugaku Zasshi, 98, 1635 (1978); J. Org. Chem., 44, 535 (1979); J. Am. Chem. Soc., 102, 6976 (1980); J. Org. Chem., 46. 164 (1981); and J. Med. Chem., 25, 1081 (1982)]:

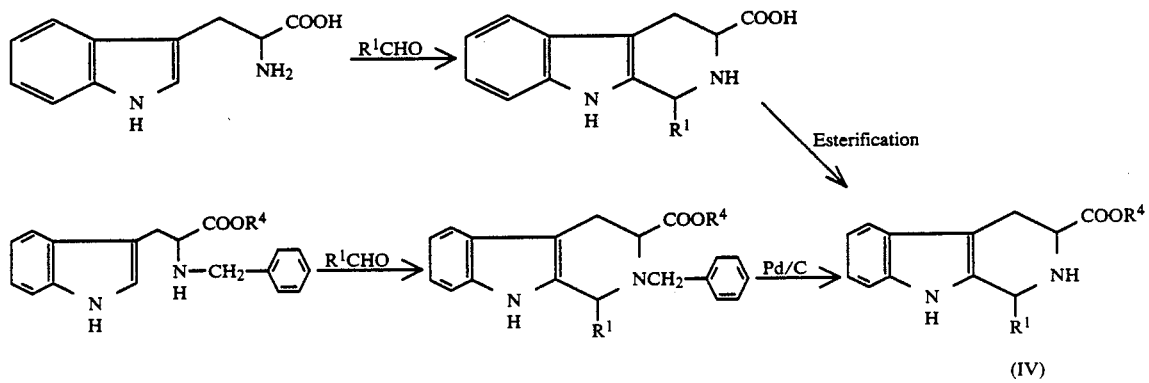

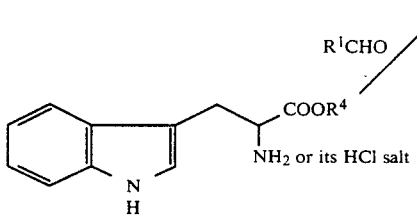

wherein $R^1$ and $R^4$ are as defined above.

The starting compound (V) may be prepared according to per se known methods as described in Chem. Pharm. Bull., 25, 1559 (1977).

There are known a variety of causal factors inducing toxic liver damage, hepatitis and fatty liver. The predominant changes observed in these diseases are necrosis of liver cells, mesenchymal reaction and accumulation of lipid. The feature of necrosis depends on the causal factor and it can be classified into centrilobular necrosis, periportal necrosis and discrete lobular necrosis. In experiment, the centrilobular necrosis is induced by carbon tetrachloride, and the degree of liver damage is determined by the measurement of liver weight and observation of the liver color with the naked eye. The periportal necrosis and the discrete lobular necrosis associated with mesenchymal reaction are induced by allyl alcohol and D-galactosamine, respectively, and the degree of liver damage is determined by the measurement of activities of glutamic-pyruvic-transaminase (GPT) and glutamic-oxaloacetic-transaminase (GOT) in the blood plasma.

The compounds (I) of the present invention have excellent activities to cure (including to prevent and alleviate) various liver diseases, particularly liver diseases associated with centrilobular necrosis, liver diseases associated with periportal necrosis, liver diseases associated with discrete lobular necrosis and mesenchymal reaction, fatty liver, drug-induced hepatopathy, and congestive hepatitis. Accordingly, the compounds of the present invention are useful as a therapeutic or prophylactic agent of hepatic diseases in animals including humans, and are used, for example, for treating or preventing various diseases such as viral hepatitis, drug-induced hepatopathy, alcoholic hepatitis, fatty liver, jaundice, and also the final symptom, i.e. hepatocirrhosis. Moreover, the compounds of the present invention also shown stimulation of the liver function with low toxicity and hence with high safety. For example, when the present compounds, methyl(3S)-3-hydroxymethyl-1,2,3,4-tetrahydro-β-carboline-2-carbodithioate, methyl(3R)-3-hydroxymethyl-1,2,3,4-tetrahydro-β-carboline-2-carbodithioate, methyl(1S,3S)-3-hydroxymethyl-1-methyl-1,2,3,4-tetrahydro-β-carboline-2-carbodithioate, or methyl(1R,3R)-3-hydroxymethyl-1-methyl-1,2,3,4-tetrahydro-β-carboline-2-carbodithioate was orally administered to mice in a dose of 1,500 mg/kg, and no mouse died during 7 days-observation after the administration. Further, the compounds (I) of the present invention have an activity of inhibiting undesirable production of lipid peroxides. Lipid peroxides levels in tissues of mammalian species are known to increase with age and cause cell death and/or damage with a consequent change of cell permeability. In addition, lipid peroxides have been suggested to be a primary etiologic factor in the genesis of stroke (cf. Stroke, Vol. 10, No. 3, pages 323-326 (1979). Thus, the compounds (I) may be used to improve the lipid peroxides levels in the tissues of the aged subjects.

When the compounds (I) and their salts of the present invention are used as a medicine, they can be administered by an oral route or parenteral route (e.g. intravenous, intramuscular or subcutaneous route). The dose of the compounds (I) and their salts may vary according to ages, weights and states of patients, severity of diseases, or the like, but is usually in the range of about 0.01 to 250 mg/kg/day, preferably 0.1 to 50 mg/kg/day. Particularly preferred dose of the present compounds (I) in the case of oral administration is in the range of about 0.1 to 250 mg/kg/day, especially 0.5 to 50 mg/kg/day.

The compounds (I) and their salts can be used in the form of conventional pharmaceutical preparations in admixture with conventional pharmaceutical carriers or diluents which are usually used for oral or parenteral preparations. The carriers include, for example, gelatine, lactose, glucose, sodium chloride, starch, magnesium stearate, talc, vegetable oils, and the like. The pharmaceutical preparations may be solid preparations such as tablets, sugar coating tablets, pills, or capsules, or liquid preparations such as solutions, suspensions, or emulsions. These preparations may be sterilized. Moreover, various auxiliaries, stabilizers, wetting agents, emulsifiers, or any other additives may optionally be added to the preparations.

The present invention is illustrated by the following Experiments and Examples, but it should not be construded to be limited thereto.

Throughout the specification and claims, the term "alkyl" denotes an alkyl having 1 to 10 carbon atoms, and the terms "lower alkyl", "lower alkoxy" and "cycloalkyl" denote an alkyl having 1 to 4 carbon atoms, an alkoxy having 1 to 4 carbon atoms, and a cycloalkyl having 5 to 6 carbon atoms, respectively.

EXPERIMENT 1

Protection against acute carbon tetrachloride-induced hepatotoxicity:

Method: The test compounds were suspended in 0.5% carboxymethyl cellulose solution, and the suspension (test compound: 100 mg/10 ml/kg) was orally administered to ddY male mice (age: 5-6 weeks old, weight: 25-30 g, one group: 3 mice), and the animals were fasted. After 3 hours, a solution of carbon tetrachloride in olive oil was orally administered in a dose of 50 μl/5 ml olive oil/kg. After 3 hours, the test compound was again orally administered in the same dose as above. Weight of the animals was measured 24 hours after CCl₄ administration, and then, the animals were killed. Immediately, the liver was taken out, weighed and macroscopically observed. As the normal control, 0.5% carboxymethyl cellulose solution and olive oil were orally administered to the animals instead of the suspension of test compound and the CCl₄ solution.

Besides, the CCl4-control group was given the CCl4 solution and 0.5% carboxymethyl cellulose solution.

The therapeutic effect of the test compounds on liver damages was evaluated based on the suppressive % of the increase of relative liver weight calculated by the following equation and also based on the macroscopic observation of the liver, as shown in Table 1. The term "relative liver weight" means weight (g) of the liver/100 g body weight.

Suppressive % of the increase of relative liver weight =

$$\left[1 - \frac{\begin{array}{c}\text{Mean of relative}\\\text{liver weight in}\\\text{test compound}\\\text{group}\end{array} - \begin{array}{c}\text{Mean of relative}\\\text{liver weight in}\\\text{normal control}\\\text{group}\end{array}}{\begin{array}{c}\text{Mean of relative}\\\text{liver weight in}\\\text{CCl}_4\text{-control}\\\text{group}\end{array} - \begin{array}{c}\text{Mean of relative}\\\text{liver weight in}\\\text{normal control}\\\text{group}\end{array}}\right] \times 100$$

TABLE 1

| Macroscopic observation of the liver | (Criteria) Suppressive % of the increase of relative liver weight | | |
|---|---|---|---|
| | ≧20% | ≧−20% to <20% | <−20% |
| Almost the same as normal control group | AA | C | D |
| Showed a sign of amelioration from CCl4—control group | A | C | D |
| Showed the same color or appearance as in CCl4—control group | B | D | D |

Remarks:
AA means "significantly effective",
A, B and C mean "effective", and D means "not effective".

The results of the above experiment are shown in the following Table 2.

TABLE 2

| | Test compound Nos. and chemical name | Evaluation (Dose: mg/kg × 2) |
|---|---|---|
| 1. | Sodium (3S)—3-hydroxymethyl-1,2,3,4-tetrahydro-β-carboline-2-carbodithioate | AA |
| 2. | Methyl (3R)—3-hydroxymethyl-1,2,3,4-tetrahydro-β-carboline-2-carbodithioate | AA |
| 3. | Methyl (3S)—3-hydroxymethyl-1,2,3,4-tetrahydro-β-carboline-2-carbodithioate | AA |
| 4. | Benzyl (3R)—3-hydroxymethyl-1,2,3,4-tetrahydro-β-carboline-2-carbodithioate | AA |
| 5. | 4-Chlorobenzyl (3S)—3-hydroxymethyl-1,2,3,4-tetrahydro-β-carboline-2-carbodithioate | AA |
| 6. | 2-Thenyl (3R)—3-hydroxymethyl-1,2,3,4-tetrahydro-β-carboline-2-carbodithioate | AA |
| 7. | 2-Thenyl (3S)—3-hydroxymethyl-1,2,3,4-tetrahydro-β-carboline-2-carbodithioate | AA |
| 8. | Methyl (1R, 3R)—3-hydroxymethyl-1-methyl-1,2,3,4-tetrahydro-β-carboline-2-carbodithioate | AA |
| 9. | Methyl (1S, 3S)—3-hydroxymethyl-1-methyl-1,2,3,4-tetrahydro-β-carboline-2-carbodithioate | AA |
| 10. | Methyl (1RS, 3SR)—trans-1-methyl-3-hydroxymethyl-1,2,3,4-tetrahydro-β-carboline-2-carbodithioate | AA |
| 11. | Methyl (1RS, 3RS)—cis-1-ethyl-3-hydroxymethyl-1,2,3,4-tetrahydro-β-carboline-2-carbodithioate | AA |
| 12. | Methyl (1RS, 3SR)—trans-1-ethyl-3-hydroxymethyl-1,2,3,4-tetrahydro-β-carboline-2-carbodithioate | AA |
| 13. | Methyl (1RS, 3RS)—cis-1,3-dihydroxymethyl-1,2,3,4-tetrahydro-β-carboline-2-carbodithioate | AA |
| 14. | Methyl (1RS, 3SR)—trans-1,3-dihydroxymethyl-1,2,3,4-tetrahydro-β-carboline-2-carbodithioate | AA |
| 15. | Methyl (3RS)—3-hydroxymethyl-1,2,3,4-tetrahydro-β-carboline-2-carbodithioate | AA |
| 16. | Ethyl (3S)—3-hydroxymethyl-1,2,3,4-tetrahydro-β-carboline-2-carbodithioate | AA |
| 17. | n-Propyl (3S)—3-hydroxymethyl-1,2,3,4-tetrahydro-β-carboline-2-carbodithioate | AA |
| 18. | n-Propyl (1S, 3S)—3-hydroxymethyl-1-methyl-1,2,3,4-tetrahydro-β-carboline-2-carbodithioate | AA |
| 19. | Ethyl (1S, 3S)—3-hydroxymethyl-1-methyl-1,2,3,4-tetrahydro-β-carboline-2-carbodithioate | AA |
| 20. | (3S)—3-Hydroxymethyl-1,2,3,4-tetrahydro-β-carboline-2-carbodithioic acid | AA |
| 21. | 4-Methoxybenzyl (3RS)—3-hydroxymethyl-1,2,3,4-tetrahydro-β-carboline-2-carbodithioate | AA |
| 22. | Methyl (1RS, 3RS)—cis-3-hydroxymethyl-1-methyl-1,2,3,4-tetrahydro-β-carboline-2-carbodithioate | AA |
| 23. | n-Butyl (1S, 3S)—3-hydroxymethyl-1-methyl-1,2,3,4-tetrahydro-β-carboline-2-carbodithioate | AA |
| 24. | Ethyl (1RS, 3SR)—trans-3-hydroxymethyl-1-ethyl-1,2,3,4-tetrahydro-β-carboline-2-carbodithioate | AA |
| 25. | Methyl (3R)—3-(2-hydroxyethyl)-1,2,3,4-tetrahydro-β-carboline-2-carbodithioate | AA |

EXPERIMENT 2

Protection against acute hepatic damage induced by allyl alcohol:

Method: The test compounds were suspended in 0.5% carboxymethyl cellulose solution, and the suspension (test compound: 300 mg/10 ml/kg) was orally administered to ddY male mice (age: 6 weeks old, weight: 27–31 g, one group: 6 mice) and the animals were fasted. After 3 hours, a solution of allyl alcohol in olive oil was orally administered in a dose of 50 μl/5 ml olive oil/kg. After 3 hours, the test compound was again orally administered in the same dose as above. 24 hours after the administration of allyl alcohol, blood was collected by cutting the carotid artery and was centrifuged to isolate blood plasma. Activities of GPT (glutamic-pyruvic-transaminase) and GOT (glutamic-oxaloacetic-transaminase) in the blood plasma were measured, and the data were expressed by Karmen unit (K.U.). As the normal control, 0.5% carboxymethyl cellulose solution and olive oil were orally administered to the animals instead of the suspension of the test compound and the allyl alcohol solution. Besides, the allyl alcohol control group was given the allyl alcohol solution and 0.5% carboxymethyl cellulose solution.

The test results are shown in the following Table 3.

TABLE 3

| | Test compounds group Test compound Nos.* | | Allyl alcohol control group | Normal control group |
|---|---|---|---|---|
| | 1 | 2 | | |
| GPT (K. U.) | 235.2 ± 75.9 | 366.6 ± 112.0 | 1027.8 ± 106.8 | 20.8 ± 2.8 |
| GOT (K. U.) | 805.1 ± 255.5 | 1084.5 ± 349.3 | 2542.6 ± 381.1 | 107.9 ± 3.7 |

*Test compound No. 1: Methyl (3S)—3-hydroxymethyl-1,2,3,4-tetrahydro-β-carboline-2-carbodithioate
Test compound No. 2: Methyl (1S, 3S)—3-hydroxymethyl-1-methyl-1,2,3,4-tetrahydro-β-carboline-2-carbodithioate

EXPERIMENT 3

Activity against acute hepatic damage induced by galactosamine:

Method: The test compounds were suspended in 0.5% carboxymethyl cellulose solution, and the suspension (test compound: 200 mg/10 ml/kg) was orally administered to Wistar male rats (age: 9 weeks old, weight: 190–220 g, one group: 5 rats) and the animals were fasted. After 3 hours, a solution of D-galactosamine in physiological saline solution was intraperitoneally administered in a dose of 250 mg/5 ml saline solution/kg. After 3 hours, the test compound was again orally administered in the same dose as above. 24 hours after administration of D-galactosamine, blood was collected from the axillary vein to kill the animals. Immediately, the liver was taken out. The plasma was isolated from the blood, and activities of GPT and GOT in the plasma were measured. Besides, lipids were extracted from the liver with an organic solvent, and the amounts of triglycerides (TG), phospholipids (PL) and total cholesterol (Tch) in the extract were measured. As the nomal control, 0.5% carboxymethyl cellulose solution and physiological saline solution were administered to the animals instead of the suspension of the test compound and the D-galactosamine solution. Besides, the D-galactosamine control group was given the D-galactosamine solution and 0.5% carboxymethyl cellulose solution.

The test results are shown in the following Table 4.

TABLE 4

| | Test compound group Test compound No. 2* | D-galactosamine control group | Normal control group |
|---|---|---|---|
| GPT (K. U.) | 317.1 ± 108.3 | 956.2 ± 267.6 | 34.0 ± 4.6 |
| GOT (K. U.) | 629.1 ± 129.0 | 1746.3 ± 424.2 | 126.2 ± 20.1 |
| TG (mg/g) | 9.9 ± 1.4 | 12.5 ± 1.7 | 5.4 ± 0.3 |
| PL (mg/g) | 38.7 ± 0.3 | 38.7 ± 1.2 | 40.9 ± 1.4 |
| Tch (mg/g) | 3.51 ± 0.10 | 3.62 ± 0.15 | 3.87 ± 0.06 |

*Test compound No. 2: The same as used in Experiment 2.

EXPERIMENT 4

Therapeutic effect against subacute hepatic damage induced by CCl₄:

Method: A mixture of the same amount of CCl₄ and olive oil was subcutaneously administered to Wistar male rats (age: 10 weeks old, weight: 200–230 g, one group: 5 rats) in a dose of 1 ml/kg (CCl₄ 0.5 ml/kg). The administration was carried out continuously once a day for 4 days. Twenty four hours after the last administration of CCl₄, a suspension of a test compound in 0.5% carboxymethyl cellulose solution was orally administered to the animals in a dose of 100 mg/10 ml/kg once a day for 4 days. 24 hours after the last administration of the test compound, blood was collected from inferior vena cava to kill the animals. Immediately, the liver was taken out. The plasma was isolated from the blood, and the activities of GPT and GOT in the plasma were measured. Besides, the amounts of TG, PL and Tch in the liver were measured, likewise. As the normal control, olive oil was administered in a dose of 0.5 ml/kg instead of a mixture of CCl₄ and olive oil, and further, 0.5% carboxymethyl cellulose solution was administered instead of the suspension of a test compound in the same dose as above. Besides, the CCl₄-control group was given the CCl₄ solution and 0.5% carboxymethyl cellulose solution.

The test results are shown in the following Table 5.

TABLE 5

| | Test compound* group | CCl₄ control group | Normal control group |
|---|---|---|---|
| GPT (K. U.) | 21.6 ± 5.6 | 58.1 ± 18.7 | 24.9 ± 1.3 |
| GOT (K. U.) | 74.4 ± 11.6 | 128.1 ± 33.8 | 79.4 ± 4.9 |
| TG (mg/g) | 36.0 ± 5.5 | 75.7 ± 6.0 | 9.3 ± 1.5 |
| PL (mg/g) | 38.8 ± 1.0 | 36.0 ± 0.5 | 38.8 ± 1.1 |
| Tch (mg/g) | 3.95 ± 0.31 | 4.81 ± 0.12 | 2.92 ± 0.15 |

*Test compound: Methyl (1S, 3S)—3-hydroxymethyl-1-methyl-1,2,3,4-tetrahydro-β-carboline-2-carbodithioate

EXPERIMENT 5

(Preventive effect on lipid peroxide formation)

0.1 ml of a dimethylsulfoxide solution containing $3 \times 10^{-3}$M of a test compound was added to a mixture of 2.4 ml of 0.067M potassium phosphate buffer solution (pH 7.4) and 0.5 ml of 10% rat brain-homogenate (final concentration of the test compound: $10^{-4}$M). After an one-hour incubation of the mixture at 37° C., one ml of 20% trichloroacetic acid was added thereto, and lipid peroxide formations were determined by the thiobarbituric acid colorimetric method (J. Robak et al., Biochem. Pharmacol., Vol. 25, page 2233 (1976)). Percentage inhibition of lipid peroxide formation of the test compound was calculated according to the following equation:

$$\text{Inhibitory \% of lipid peroxide formation} = \left[1 - \frac{\Delta OD \text{ of test tube*}}{\Delta OD \text{ of control tube**}}\right] \times 100$$

Note:
*Tube containing the test compound
**Tube containing an equal volume of dimethylsulfoxide instead of the test compound solution
$\Delta OD$ was calculated as [(optical density measured at 532 nm) − (optical density measured at 600 nm)]

The results are shown in the following Table 6.

TABLE 6

| Test compound Nos.* | Inhibitory % of lipid peroxide formation |
|---|---|
| 4 | 94.4 |
| 6 | 93.7 |
| 7 | 93.6 |
| 9 | 96.8 |
| 11 | 91.9 |
| 12 | 90.2 |
| 17 | 93.1 |

TABLE 6-continued

| Test compound Nos.* | Inhibitory % of lipid peroxide formation |
| --- | --- |
| 18 | 95.9 |
| 19 | 94.1 |
| 21 | 94.8 |
| 23 | 96.2 |
| 24 | 95.6 |

*Test compounds were the same as used in Experiment 1.

EXAMPLE 1

Sodium (3S)-3-hydroxymethyl-1,2,3,4-tetrahydro-β-carboline-2-carbodithioate:

To a mixture of (3S)-3-hydroxymethyl-1,2,3,4-tetrahydro-β-carboline (5.06 g), CS$_2$ (2.0 g) and ethanol (230 ml) is added dropwise a 1N NaOH solution (25 ml) at room temperature. The mixture is stirred for 2 hours, and thereto is added ethanol. The precipitated crystals are collected by filtration and recrystallized from water-ethanol to give the title compound (5.3 g, 71%) as colorless needles, m.p. 209°–210° C. (decomp.), $[\alpha]_D^{20}+151.8°$ (c=1, methanol).

Anal: Calcd. for C$_{13}$H$_{13}$N$_2$OS$_2$Na.½H$_2$O: C,49.06; H,4.75; N,8.80; S,20.15. Found: C,48.90; H,4.92; N,8.92; S,20.00. Mass m/e: 244 (M$^+$—NaSH).

EXAMPLE 2

Methyl (3S)-3-hydroxymethyl-1,2,3,4-tetrahydro-β-carboline-2-carbodithioate:

(3S)-3-Hydroxymethyl-1,2,3,4-tetrahydro-β-carboline (30.3 g) is dissolved in a mixture of methanol (300 ml) and water (80 ml), and thereto are added triethylamine (15.9 g) and CS$_2$ (11.9 g). The mixture is stirred at 20° C. for 30 minutes, and thereto is added dropwise methyl iodide (22.35 g). The mixture is stirred at 20°–25° C. for 1.5 hour and distilled to remove the solvent. The residue is dissolved in ethyl acetate and washed with 5% HCl and water, dried over sodium sulfate and distilled to remove the solvent. The residue is recrystallized from aqueous ethanol to give the title compound (42.0 g, 90%) as colorless needles, m.p. 114°–116° C., $[\alpha]_D^{20}+159.0°$ (c=1, methanol). NMR (CDCl$_3$, δ): 2.62 (s, 3H, CSSCH$_3$), Mass m/e: 292 (M$^+$), 244 (M$^+$—CH$_3$SH).

EXAMPLE 3

Methyl (3R)-3-hydroxymethyl-1,2,3,4-tetrahydro-β-carboline-2-carbodithioate:

In the same manner as described in Example 2 by using (3R)-3-hydroxymethyl-1,2,3,4-tetrahydro-β-carboline (22.58 g), triethylamine (15.7 ml), CS$_2$ (6.93 ml), methyl iodide (7.16 ml) and 70% ethanol (340 ml), there is prepared the title compound (28.7 g, 88%) as colorless needles, m.p. 106°–108° C. (recrystallized from aqueous ethanol), $[\alpha]_D^{20}-158.6°$ (c=1.0, methanol). NMR (CDCl$_3$, δ): 2.67 (s, 3H, CSSCH$_3$), Mass m/e: 292 (M$^+$), 244 (M$^+$—CH$_3$SH).

EXAMPLE 4

Methyl (3RS)-3-hydroxymethyl-1,2,3,4-tetrahydro-β-carboline-2-carbodithioate:

In the same manner as described in Example 2 by using (3RS)-3-hydroxymethyl-1,2,3,4-tetrahydro-β-carboline (2.02 g), triethylamine (1.4 ml), CS$_2$ (0.68 ml), methyl iodide (0.68 ml) and 70% ethanol (30 ml), there is prepared the title compound (2.63 g, 90%) as colorless prisms, m.p. 172°–173° C. (recrystallized from aqueous ethanol).

NMR (CDCl$_3$, δ): 2.65 (s, 3H, CSSCH$_3$), Mass m/e: 292 (M$^+$), 244 (M$^+$—CH$_3$SH).

EXAMPLE 5

Ethyl (3S)-3-hydroxymethyl-1,2,3,4-tetrahydro-β-carboline-2-carbodithioate:

In the same manner as described in Example 2 by using (3S)-3-hydroxymethyl-1,2,3,4-tetrahydro-β-carboline (2.02 g), triethylamine (1.52 g), CS$_2$ (1.14 g), ethyl iodide (2.34 g), ethanol (25 ml) and water (5 ml), there is prepared the title compound (2.0 g, 65%) as colorless needles, m.p. 74°–76° C. (recrystallized from ethanol), $[\alpha]_D^{20}+146.0°$ (c=1, methanol). NMR (CDCl$_3$, δ): 1.35 (t, J=7.5 Hz, 3H, CSSCH$_2$CH$_3$), 3.36 (q, J=7.5 Hz, 2H, CSSCH$_2$CH$_3$), Mass m/e: 306 (M$^+$), 244 (M$^+$-thioethanol).

EXAMPLE 6 n-Propyl (3S)-3-hydroxymethyl-1,2,3,4-tetrahydro-β-carboline-2-carbodithioate:

In the same manner as described in Example 2 by using (3S)-3-hydroxymethyl-1,2,3,4-tetrahydro-carboline (1.5 g), triethylamine (1.5 g), CS$_2$ (1.13 g), n-propyl iodide (2.52 g), tetrahydrofuran (11 ml) and water (2 ml), there is prepared the title compound (1.50 g, 63%) as colorless prisms, m.p. 130°–131° C. (recrystallized from aqueous ethanol), $[\alpha]_D^{20}+141.8°$ (c=1, methanol).

NMR (CDCl$_3$, δ): 1.00 (t, J=7.0 Hz, 3H, CSSCH$_2$CH$_2$CH$_3$), Mass m/e: 320 (M$^+$), 244 (M$^+$-n-thiopropanol).

EXAMPLE 7

Butyl (3S)-3-hydroxymethyl-1,2,3,4-tetrahydro-β-carboline-2-carbodithioate:

In the same manner as described in Example 2 by using (3S)-3-hydroxymethyl-1,2,3,4-tetrahydro-β-carboline (2.02 g), triethylamine (1.52 g), CS$_2$ (1.14 g), n-butyl iodide (2.97 g), methanol (25 ml) and water (5 ml), there is prepared the title compound (2.0 g, 60%) as colorless needles, m.p. 60°–63° C. (recrystallized from ethanol), $[\alpha]_D^{20}+133.6°$ (c=1.0, methanol). NMR (CDCl$_3$, δ): 0.93 (m, 3H, CSS(CH$_2$)$_3$CH$_3$), Mass m/e: 334 (M$^+$), 244 (M$^+$-n-thiobutanol).

EXAMPLE 8

Benzyl (3R)-3-hydroxymethyl-1,2,3,4-tetrahydro-β-carboline-2-carbodithioate:

(3R)-3-Hydroxymethyl-1,2,3,4-tetrahydro-β-carboline (1.01 g) is dissolved in 70% ethanol (20 ml), and thereto is added dropwise 2N KOH (2.5 ml) and is further added CS$_2$ (0.30 ml). The mixture is stirred at room temperature for 30 minutes, and thereto is added dropwise benzyl bromide (0.86 g). The mixture is stirred at room temperature for 4 hours and distilled to remove the solvent. The residue is dissolved in ethyl acetate, and the solution is washed with 10% HCl and water in order, dried over sodium sulfate, and distilled to remove the solvent. The residue is purified with silica gel column chromatography (solvent: CHCl$_3$:methanol=10:1) to give the title compound (1.29 g, 70%) as white powder, $[\alpha]_D^{20}-117.3°$ (c=0.99, methanol). NMR (CDCl$_3$,δ): 4.58 (s, 2H, CSSCH$_2$C$_6$H$_5$), Mass m/e: 368 (M$^+$), 244 (M$^+$—C$_6$H$_5$CH$_2$SH).

EXAMPLE 9

4-Chlorobenzyl (3S)-3-hydroxymethyl-1,2,3,4-tetrahydro-β-carboline-2-carbodithioate:

In the same manner as described in Example 8 by using (3S)-3-hydroxymethyl-1,2,3,4-tetrahydro-β-carboline (202 mg), 2N NaOH (0.5 ml), $CS_2$ (0.06 ml), 4-chlorobenzyl chloride (0.16 g) and 70% ethanol (5 ml), there is prepared the title compound (270 mg, 67%) as colorless needles, m.p. 175°–176° C. (recrystallized from ethyl acetate-n-hexane), $[\alpha]_D^{20} +94.4°$ (c=1.0, methanol).

NMR (CDCl$_3$-DMSO-d$_6$, δ): 4.57 (s, 2H, CSSCH$_2$C$_6$H$_4$-p-Cl), Mass m/e: 402 (M+), 244 (M+-p-Cl-C$_6$H$_4$CH$_2$SH).

EXAMPLE 10

4-Chlorobenzyl (3R)-3-hydroxymethyl-1,2,3,4-tetrahydro-β-carboline-2-carbodithioate:

In the same manner as described in Example 8 by using (3R)-3-hydroxymethyl-1,2,3,4-tetrahydro-β-carboline (1.01 g), 2N KOH (2.5 ml), $CS_2$ (0.3 ml), 4-chlorobenzyl chloride (0.81 g) and 70% ethanol (20 ml), there is prepared the title compound (1.34 g, 67%) as white powder, $[\alpha]_D^{20} -111.8°$ (c=1.0, methanol). NMR (CDCl$_3$-DMSO-d$_6$, δ): 4.56 (s, 2H, CSSCH$_2$C$_6$H$_4$-p-Cl), Mass m/e: 402 (M+), 244 (M+-p-Cl-C$_6$H$_4$CH$_2$SH).

EXAMPLE 11

2-Thenyl (3S)-3-hydroxymethyl-1,2,3,4-tetrahydro-β-carboline-2-carbodithioate:

In the same manner as described in Example 8 by using (3S)-3-hydroxymethyl-1,2,3,4-tetrahydro-β-carboline (2.02 g), 2N NaOH (10 ml), $CS_2$ (1.5 g), 2-Thenyl chloride (2.65 g), and 80% ethanol (50 ml), there is prepared the title compound (1.86 g, 50%) as white powder, $[\alpha]_D^{20} +108.4°$ (c=1.0, methanol). NMR (CDCl$_3$, δ): 4.84 (s, 2H, CSSCH$_2$—

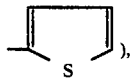

Mass m/e: 374 (M+), 244 (M+—

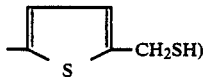

EXAMPLE 12

2-Thenyl (3R)-3-hydroxymethyl-1,2,3,4-tetrahydro-β-carboline-2-carbodithioate:

In the same manner as described in Example 8 by using (3R)-3-hydroxymethyl-1,2,3,4-tetrahydro-β-carboline (2.02 g), 2N NaOH (12.5 ml), $CS_2$ (1.9 g), 2-thenyl chloride (3.31 g) and 80% ethanol (50 ml), there is prepared the title compound (1.68 g, 45%) as white powder, $[\alpha]_D^{20} -113.8°$ (c=1.0, methanol). NMR (CDCl$_3$, δ): 4.83 (s, 2H,

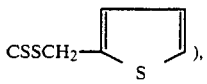

Mass m/e: 374 (M+), 244 (M+—

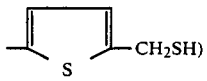

EXAMPLE 13

Methyl (1S, 3S)-3-hydroxymethyl-1-methyl-1,2,3,4-tetrahydro-β-carboline-2-carbodithioate:

To a mixture of (1S, 3S)-3-hydroxymethyl-1-methyl-1,2,3,4-tetrahydro-β-carboline (30.5 g), triethylamine (28.54 g), ethanol (800 ml) and water (180 ml) is added $CS_2$ (21.47 g), and the mixture is stirred at room temperature for 30 minutes, and thereto is added dropwise methyl iodide (40.04 g). The mixture is stirred at the same temperature for 2 hours and then distilled under reduced pressure to remove the solvent. The residue is dissolved in ethyl acetate, and the solution is washed with water, 5% HCl and water, dried over sodium sulfate and distilled to remove the solvent. The residue is dissolved in ethanol (100 ml), and the solution is added dropwise to water (1.5 liter). The precipitated crystals are collected by filtration and dried to give the title compound (37 g, 86%) as white powder, $[\alpha]_D^{20} +209.1°$ (c=1.0, methanol).

NMR (CDCl$_3$, δ): 1.68 (d, J=6.8 Hz), 3H, C$_1$—CH$_3$), 2.72 (s, 3H, CSSCH$_3$), Mass m/e: 306 (M+), 258 (M+—CH$_3$SH).

EXAMPLE 14

Methyl (1R, 3R)-3-hydroxymethyl-1-methyl-1,2,3,4-tetrahydro-β-carboline-2-carbodithioate:

In the same manner as described in Example 13 by using (1R, 3R)-3-hydroxymethyl-1-methyl-1,2,3,4-tetrahydro-β-carboline (4.32 g), triethylamine (4.04 g), $CS_2$ (3.04 g), methyl iodide (5.68 g) and 80% ethanol (150 ml), there is prepared the title compound (4.22 g, 69%) as white powder, $[\alpha]_D^{20} -205.4°$ (c=1.0, methanol). NMR (CDCl$_3$, δ): 1.66 (d, J=6.7 Hz, 3H, C$_1$—CH$_3$), 2.70 (s, 3H, CSSCH$_3$), Mass m/e: 306 (M+), 258 (M+—CH$_3$SH).

EXAMPLE 15

Methyl (1RS, 3SR)-trans-3-hydroxymethyl-1-methyl-1,2,3,4-tetrahydro-β-carboline-2-carbodithioate:

In the same manner as described in Example 13 by using (1RS, 3SR)-trans-3-hydroxymethyl-1-methyl-1,2,3,4-tetrahydro-β-carboline (1.08 g), triethylamine (1.01 g), $CS_2$ (760 mg), methyl iodide (1.42 g) and dimethylsulfoxide (10 ml), there is prepared the title compound (1.22 g, 79.7%) as colorless needles, m.p. 153°–156° C. (recrystallized from aqueous methanol). NMR (CDCl$_3$, δ): 2.60 (d, J=7.0 Hz, 3H, C$_1$—CH$_3$), 2.68 (s, 3H, CSSCH$_3$), Mass m/e: 306 (M+), 258 (M+—CH$_3$SH).

EXAMPLE 16

Ethyl (1S, 3S)-3-hydroxymethyl-1-methyl-1,2,3,4-tetrahydro-β-carboline-2-carbodithioate:

In the same manner as described in Example 13 by using (1S, 3S)-3-hydroxymethyl-1-methyl-1,2,3,4-tetrahydro-β-carboline (1.08 g), triethylamine (1.01 g), $CS_2$ (0.76 g), ethyl iodide (1.56 g), methanol (25 ml) and water (2.5 ml), there is prepared the title compound (1.25 g, 78%) as white powder, $[\alpha]_D^{20}+176.0°$ (c=1, methanol). NMR ($CDCl_3$, δ): 1.38 (t, J=7.3 Hz, 3H, $CSSCH_2CH_3$), 1.62 (d, J=6.8 Hz, 3H, $C_1$—$CH_3$), Mass m/e: 320 ($M^+$), 291 ($M^+$—$C_2H_5$), 258 ($M^+$—$C_2H_5SH$).

EXAMPLE 17 n-Propyl (1S, 3S)-3-hydroxymethyl-1-methyl-1,2,3,4-tetrahydro-β-carboline-2-carbodithioate:

In the same manner as described in Example 13 by using (1S, 3S)-3-hydroxymethyl-1-methyl-1,2,3,4-tetrahydro-β-carboline (1.08 g), triethylamine (1.01 g), $CS_2$ (0.76 g), n-propyl iodide (1.7 g), ethanol (20 ml) and water (4 ml), there is prepared the title compound (1.26 g, 76%) as colorless needles, m.p. 115°–118° C. (recrystallized from ethanol), $[\alpha]_D^{20}+184.4°$ (c=1.0, methanol).

NMR ($CDCl_3$, δ): 1.06 (t, J=7.0 Hz, 3H, $CSSCH_2CH_2CH_3$), 1.65 (d, J=6.6 Hz, 3H, $C_1$—$CH_3$), Mass m/e: 334 ($M^+$), 291 ($M^+$—n—$C_3H_7$), 258 ($M^+$—n—$C_3H_7SH$).

EXAMPLE 18

4-Chlorobenzyl (1S, 3S)-3-hydroxymethyl-1-methyl-1,2,3,4-tetrahydro-β-carboline-2-carbodithioate:

In the same manner as described in Example 13 by using (1S,3S)-3-hydroxymethyl-1-methyl-1,2,3,4-tetrahydro-β-carboline (216 mg), 2N NaOH (1.5 ml), $CS_2$ (228 mg), 4-chlorobenzyl chloride (480 mg) and 80% ethanol (5 ml), there is prepared the title compound (292 mg, 70%) as white powder, $[\alpha]_D^{20}+136.4°$ (c=1.1, methanol). NMR ($CDCl_3$, δ): 1.63 (d, J=6.5 Hz, 3H, $C_1$—$CH_3$), 4.57 (s, 2H, $CSSCH_2$-$C_6H_4$-p-Cl), Mass m/e: 291 ($M^+$-$CH_2C_6H_4$-p-Cl), 258 ($M^+$-p-Cl-$C_6H_4$-$CH_2SH$).

EXAMPLE 19

Methyl (1RS, 3RS)-cis-1-ethyl-3-hydroxymethyl-1,2,3,4-tetrahydro-β-carboline-2-carbodithioate:

In the same manner as described in Example 13 by using (1RS, 3RS)-cis-1-ethyl-3-hydroxymethyl-1,2,3,4-tetrahydro-β-carboline (1.04 g), triethylamine (2.73 g), $CS_2$ (2.05 g), methyl iodide (3.84 g), methanol (30 ml) and water (3 ml), there is prepared the title compound (940 mg, 65%) as colorless prisms, m.p. 177°–180° C. (recrystallized from ether). NMR ($CDCl_3$, δ): 1.34 (t, J=7.0 Hz, 3H, $C_1$—$CH_2CH_3$), 2.70 (s, 3H, $CSSCH_3$), Mass m/e: 320 ($M^+$), 272 ($M^+$—$CH_3SH$).

EXAMPLE 20

Methyl (1RS, 3SR)-trans-1-ethyl-3-hydroxymethyl-1,2,3,4-tetrahydro-β-carboline-2-carbodithioate:

In the same manner as described in Example 13 by using (1RS, 3SR)-trans-1-ethyl-3-hydroxymethyl-1,2,3,4-tetrahydro-β-carboline (300 mg), triethylamine (330 mg), $CS_2$ (250 mg), methyl iodide (460 mg) and dimethylsulfoxide (3 ml), there is prepared the title compound (320 mg, 77%) as colorless needles, m.p. 170°–172° C. (recrystallized from aqueous ethanol). NMR ($CDCl_3$, δ): 0.85 (t, J=7.0 Hz, 3H, $C_1$—$CH_2CH_3$), 2,68 (s, 3H, $CSSCH_3$), Mass m/e: 320 ($M^+$), 272 ($M^+$—$CH_3SH$).

EXAMPLE 21

Methyl (1RS, 3RS)-cis-1-butyl-3-hydroxymethyl-1,2,3,4-tetrahydro-β-carboline-2-carbodithioate:

In the same manner as described in Example 13 by using (1RS, 3RS)-cis-1-butyl-3-hydroxymethyl-1,2,3,4-tetrahydro-β-carboline (1.05 g), triethylamine (0.53 g), $CS_2$ (0.50 g), methyl iodide (0.95 g) and dimethylsulfoxide (8 ml), there is prepared the title compound (0.85 g, 61%) as white powder. NMR ($CDCl_3$, δ): 0.96 (t, J=7.0 Hz, 3H, $C_1$—$(CH_2)_3CH_3$), 2.72 (s, 3H, $CSSCH_3$), Mass m/e: 348 ($M^+$), 300 ($M^+$—$CH_3SH$).

EXAMPLE 22

Methyl (1RS, 3SR)-trans-1-butyl-3-hydroxymethyl-1,2,3,4-tetrahydro-β-carboline-2-carbodithioate:

In the same manner as described in Example 13 by using (1RS, 3SR)-trans-1-butyl-3-hydroxyemthyl-1,2,3,4-tetrahydro-β-carboline (1.0 g), triethylamine (0.78 g), $CS_2$ (0.59 g), methyl iodide (1.1 g) and dimethylsulfoxide (8 ml), there is prepared the title compound (0.95 g, 70%) as white powder. NMR ($CDCl_3$, δ): 0.84 (t, J=7.0 Hz, 3H, $C_1$—$(CH_2)_3CH_3$), 2.70 (s, 3H, $CSSCH_3$), Mass m/e: 348 ($M^+$), 300 ($M^+$—$CH_3SH$).

EXAMPLE 23

Methyl (1RS, 3RS)-cis-1,3-dihydroxymethyl-1,2,3,4-tetrahydro-β-carboline-2-carbodithioate:

In the same manner as described in Example 13 by using (1RS, 3RS)-cis-1,3-dihydroxymethyl-1,2,3,4-tetrahydro-β-carboline (0.70 g), triethylamine (0.84 ml), $CS_2$ (0.36 ml), methyl iodide (0.37 ml) and dimethylsulfoxide (6 ml), there is prepared the title compound (369 mg, 38%) as white powder. NMR ($CDCl_3$, δ): 2.66 (s, 3H, $CSSCH_3$), Mass m/e: 322 ($M^+$), 304 ($M^+$—$H_2O$), 274 ($M^+$—$CH_3SH$).

EXAMPLE 24

Methyl (1RS, 3SR)-trans-1,3-dihydroxymethyl-1,2,3,4-tetrahydro-β-carboline-2-carbodithioate:

In the same manner as described in Example 13 by using (1RS, 3SR)-trans-1,3-dihydroxymethyl-1,2,3,4-tetrahydro-β-carboline (0.65 g), triethylamine (0.79 ml), $CS_2$ (0.34 ml), methyl iodide (0.35 ml) and dimethylsulfoxide (6 ml), there is prepared the title compound (350 mg, 39%) as colorless needles, m.p. 179°–180° C. (recrystallized from water-ethanol). NMR ($CDCl_3$-$DMSO$-$d_6$, δ): 2.66 (s, 3H, $CSSCH_3$), Mass m/e: 304 ($M^+$—$H_2O$), 274 ($M^+$—$CH_3SH$).

EXAMPLE 25

Methyl (1RS, 3RS)-cis-1-cyclohexyl-3-hydroxymethyl-1,2,3,4-tetrahydro-β-carboline-2-carbodithioate:

In the same manner as described in Example 13 by using (1RS, 3RS)-cis-1-cyclohexyl-3-hydroxymethyl-1,2,3,4-tetrahydro-β-carboline (569 mg) [J.A.C.S. 102, 6976 (1980)], triethylamine (405 mg), $CS_2$ (304 mg), methyl iodide (568 mg) and dimethylsulfoxide (5 ml), there is prepared the title compound (490 mg, 65%) as white powder. NMR ($CDCl_3$, δ): 2.63 (s, 3H, $CSSCH_3$), Mass m/e: 374 ($M^+$), 326 ($M^+$—$CH_3SH$).

EXAMPLE 26

Methyl (1RS, 3RS)-cis-3-hydroxymethyl-1-phenyl-1,2,3,4-tetrahydro-β-carboline-2-carbodithioate:

In the same manner as described in Example 13 by using (1RS, 3RS)-cis-3-hydroxymethyl-1-phenyl-1,2,3,4-tetrahydro-β-carboline (300 mg) [J.A.C.S., 102, 6976 (1980)], triethylamine (220 mg), CS$_2$ (160 mg), methyl iodide (306 mg) and dimethylsulfoxide (6 ml), there is prepared the title compound (310 mg, 78%) as white powder.

NMR (CDCl$_3$, δ): 2.72 (s, 3H, CSSCH$_3$), Mass m/e: 368 (M$^+$), 320 (M$^+$—CH$_3$SH).

EXAMPLE 27

4-Chlorobenzyl (3R)-3-(2-hydroxyethyl)-1,2,3,4-tetrahydro-β-carboline-2-carbodithioate:

In the same manner as described in Example 13 by using (3R)-3-(2-hydroxyethyl)-1,2,3,4-tetrahydro-β-carboline (100 mg), 2N NaOH (0.23 ml), CS$_2$ (0.028 ml), 4-chlorobenzyl chloride (82 mg) and 70% ethanol (2.5 ml), there is prepared the title compound (66 mg, 34%) as white powder, $[\alpha]_D^{20}$ −115.8° (c=1.0, ethyl acetate). Mass m/e: 416 (M$^+$), 258 (M$^+$—p—Cl—C$_6$H$_4$—CH$_2$SH).

EXAMPLE 28

(3S)-3-Hydroxymethyl-1,2,3,4-tetrahydro-β-carboline-2-carbodithioic acid:

(3S)-3-Hydroxymethyl-1,2,3,4-tetrahydro-β-carboline (2.02 g) is dissolved in dimethylsulfoxide (10 ml), and thereto are added triethylamine (1.67 ml) and CS$_2$ (0.72 ml), and the mixture is stirred at room temperature for 3 hours. The reaction mixture is poured onto ice-water and is neutralized with 10% HCl. The precipitated crystals are collected by filtration, washed with water and then recrystallized from methanol to give the title compound (1.46 g, 60%) as colorless needles, m.p. 225°-227° C. IR $\nu_{max}^{Nujol}$ (cm$^{-1}$): 3480, 3340; Mass m/e: 278 (M$^+$), 244 (M$^+$—H$_2$S); $[\alpha]_D^{20}$+170.0° (c=1.0, methanol).

EXAMPLE 29 n-Hexyl (3S)-3-hydroxymethyl-1,2,3,4-tetrahydro-β-carboline-2-carbodithioate:

(3S)-3-Hydroxymethyl-1,2,3,4-tetrahydro-β-carboline (2.02 g) is dissolved in dimethylsulfoxide (10 ml), and thereto are added triethylamine (1.67 ml) and CS$_2$ (0.72 ml), and the mixture is stirred at room temperature for 20 minutes. To the reaction mixture is added dropwise n-hexyl bromide (1.98 g), and the mixture is stirred at room temperature for 2.5 hours. The reaction mixture is poured onto ice-water and the mixture is extracted with ethyl acetate. The ethyl acetate layer is washed with water, dried over sodium sulfate, and then distilled to remove the solvent. The residue is recrystallized from ether-n-hexane to give the title compound (2.65 g, 73.2%) as colorless needles, m.p. 102°-106° C. NMR (CDCl$_3$, δ): 0.90 (broad, t, 3H, —(CH$_2$)$_5$—CH$_3$); Mass m/e: 362 (M$^+$), 244 (M$^+$—C$_6$H$_{13}$SH); $[\alpha]_D^{20}$+130.0° (c=1.0, methanol).

EXAMPLE 30 n-Decyl (3S)-3-hydroxymethyl-1,2,3,4-tetrahydro-β-carboline-2-carbodithioate:

In the same manner as described in Example 29 by using (3S)-3-hydroxymethyl-1,2,3,4-tetrahydro-β-carboline (2.02 g), triethylamine (1.67 ml), CS$_2$ (0.72 ml), n-decyl bromide (2.65 g) and dimethylsulfoxide (10 ml), there is prepared the title compound (2,48 g, 59%) as colorless needles, m.p. 115°-118° C. (recrystallized from ether-n-hexane), $[\alpha]_D^{20}$+113.0° (c=1.0, methanol); NMR (CDCl$_3$, δ): 0.95 (m, 3H, —CH$_3$); Mass m/e: 418 (M$^+$), 244 (M$^+$—C$_{10}$H$_{21}$SH).

EXAMPLE 31

4-(N-Formylamino)benzyl (3S)-3-hydroxymethyl-1,2,3,4-tetrahydro-β-carboline-2-carbodithioate:

In the same manner as described in Example 29 by using (3S)-3-hydroxymethyl-1,2,3,4-tetrahydro-β-carboline (1.21 g), triethylamine (0.84 ml), CS$_2$ (0.36 ml), 4-(N-formylamino)benzyl chloride (1.02 g) and dimethylsulfoxide (30 ml), there is prepared the title compound (1.43 g, 58%) as pale yellow powder, $[\alpha]_D^{20}$+120.2° (c=1.0, dimethylformamide); NMR (DMSO-d$_6$, δ): 4.54 (s, 2H,

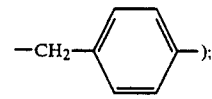

Mass m/e: 244 (M$^+$—

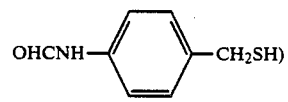

EXAMPLE 32

4-Nitrobenzyl (3RS)-3-hydroxymethyl-1,2,3,4-tetrahydro-β-carboline-2-carbodithioate:

In the same manner as described in Example 29 by using (3RS)-3-hydroxymethyl-1,2,3,4-tetrahydro-β-carboline (1.01 g), triethylamine (0.77 ml), CS$_2$ (0.33 ml), 4-nitrobenzyl chloride (1.08 g) and 80% methanol (20 ml), there is prepared the title compound (1.47 g, 71%) as pale yellow needles, m.p. 193°-194° C. (recrystallized from aqueous methanol), NMR (DMSO-d$_6$, δ): 4.79 (s, 2H,

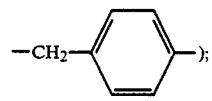

Mass m/e: 244 (M$^+$—

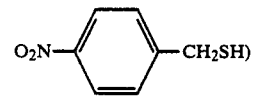

EXAMPLE 33

4-Methoxybenzyl (3RS)-3-hydroxymethyl-1,2,3,4-tetrahydro-β-carboline-2-carbodithioate:

In the same manner as described in Example 29 by using (3RS)-3-hydroxymethyl-1,2,3,4-tetrahydro-β-carboline (1.01 g), triethylamine (0.7 ml), CS$_2$ (0.3 ml), 4-methoxybenzyl chloride (1.0 g) and dimethylsulfoxide (5 ml), there is prepared the title compound (1.41 g, 71%) as white powder, NMR (CDCl$_3$+DMSO-d$_6$, δ): 4.52 (s, 2H,

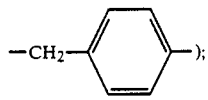

Mass m/e: 398 (M+), 244 (M+—

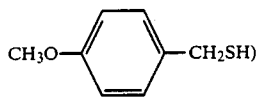

CH₃O— —CH₂SH)

EXAMPLE 34

Methyl (1RS, 3RS)-cis-3-hydroxymethyl-1-methyl-1,2,3,4-tetrahydro-β-carboline-2-carbodithioate:

(1RS, 3RS)-cis-3-Hydroxymethyl-1-methyl-1,2,3,4-tetrahydro-β-carboline (4.326 g) is dissolved in dimethylsulfoxide (20 ml), and thereto are added CS₂ (2.4 ml) and triethylamine (5.6 ml). The mixture is stirred at room temperature for 30 minutes, and thereto is added dropwise methyl iodide (2.5 ml), and the mixture is stirred at room temperature for 2 hours. The reaction mixture is poured onto ice-water, and the mixture is extracted with ethyl acetate. The extract is washed with water, 5% HCl and water in order, dried over sodium sulfate and then distilled to remove the solvent. The residue is recrystallized from aqueous ethanol to give the title compound (5.5 g, 90%) as colorless needles, m.p. 164°–166° C., NMR (CDCl₃, δ): 1.68 (d, J=6.8 Hz, 3H, C₁—CH₃), 2.73 (s, 3H, CSSCH₃); Mass m/e: 306 (M+), 258 (M+—CH₃SH).

EXAMPLE 35 n-Butyl (1S, 3S)-3-hydroxymethyl-1-methyl-1,2,3,4-tetrahydro-β-carboline-2-carbodithioate:

In the same manner as described in Example 34 by using (1S, 3S)-3-hydroxymethyl-1-methyl-1,2,3,4-tetrahydro-β-carboline (1.08 g), triethylamine (1.01 g), CS₂ (0.76 g), n-butyl iodide (1.84 g) and dimethylformamide (8 ml), there is prepared the title compound (1.3 g, 75%) as colorless needles, m.p. 110°–113° C. (recrystallized from aqueous ethanol, [α]_D^20 +181.8° (c=1.0, methanol); NMR (CDCl₃, δ): 0.97 (m, 3H, —(CH₂)₃C$\underline{H_3}$); Mass m/e: 348 (M+), 258 (M+—C₄H₉SH).

EXAMPLE 36

4-Methylbenzyl (1S, 3S)-3-hydroxymethyl-1-methyl-1,2,3,4-tetrahydro-β-carboline-2-carbodithioate:

In the same manner as described in Example 34 by using (1S, 3S)-3-hydroxymethyl-1-methyl-1,2,3,4-tetrahydro-β-carboline (1.08 g), triethylamine (1.01 g), CS₂ (0.76 g), 4-methylbenzyl chloride (1.4 g) and dimethylsulfoxide (10 ml), there is prepared the title compound (1.58 g, 80%) as white powder, [α]_D^20 +63.2° (c=0.5, methanol); NMR (CDCl₃, δ): 2.31 (s, 3H,

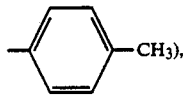

4.66 (s, 2H,

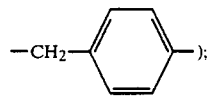

Mass m/e: 396 (M+), 258 (M+—

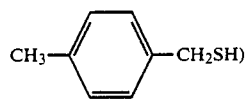

CH₃— —CH₂SH)

EXAMPLE 37

4-Methoxybenzyl (1RS, 3RS)-cis-3-hydroxymethyl-1-methyl-1,2,3,4-tetrahydro-β-carboline-2-carbodithioate:

In the same manner as described in Example 34 by using (1RS, 3RS)-cis-3-hydroxymethyl-1-methyl-1,2,3,4-tetrahydro-β-carboline (2.16 g), triethylamine (1.4 ml), CS₂ (0.60 ml), 4-methoxybenzyl chloride (2.01 g) and dimethylsulfoxide (10 ml), there is prepared the title compound (3.0 g, 73%) as colorless needles, m.p. 152°–153° C. (recrystallized from aqueous ethanol), NMR (CDCl₃, δ): 3.79 (s, 3H,

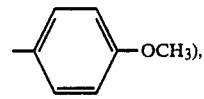

4.57 (s, 2H,

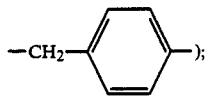

Mass m/e: 412 (M+), 258 (M+—

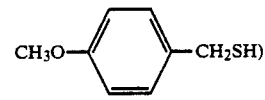

CH₃O— —CH₂SH)

EXAMPLE 38

2-Phenylethyl (1RS, 3RS)-cis-3-hydroxymethyl-1-methyl-1,2,3,4-tetrahydro-β-carboline-2-carbodithioate:

In the same manner as described in Example 34 by using (1RS, 3RS)-cis-3-hydroxymethyl-1-methyl-1,2,3,4-tetrahydro-β-carboline (1.08 g), triethylamine (0.7 ml), CS₂ (0.3 ml), 2-phenylethyl bromide (0.93 g) and dimethylsulfoxide (5 ml), there is prepared the title compound (1.88 g, 95%) as pale yellow powder, NMR (CDCl₃, δ): 3.65 (b, t, J=6.0 Hz, 2H,

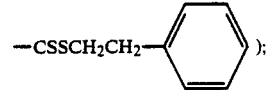

Mass m/e: 396 (M+), 258 (M+—

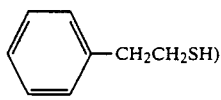

EXAMPLE 39

Ethyl (1RS, 3SR)-trans-1-ethyl-3-hydroxymethyl-1,2,3,4-tetrahydro-β-carboline-2-carbodithioate:

(1RS, 3SR)-trans-1-Ethyl-3-hydroxymethyl-1,2,3,4-tetrahydro-β-carboline (0.461 g) is dissolved in dimethylsulfoxide (2 ml), and thereto are added $CS_2$ (0.27 ml) and triethylamine (0.61 ml). The mixture is stirred at room temperature for one hour, and thereto is added dropwise ethyl iodide (0.38 ml), and the mixture is stirred at room temperature for 2 hours. The reaction mixture is poured onto ice-water, and the mixture is extracted with ethyl acetate. The extract is washed with water, dried over sodium sulfate and then distilled to remove the solvent. The residue is recrystallized from aqueous ethanol to give the title compound (0.477 g, 71%) as colorless needles, m.p. 82°–84° C., NMR ($CDCl_3$, δ): 1.40 (t, J=7.0 Hz, 3H, $CSSCH_2CH_3$); Mass m/e: 334 (M+), 272 (M+—$CH_3CH_2SH$).

EXAMPLE 40

Methyl (1RS, 3RS)-cis-1-propyl-3-hydroxymethyl-1,2,3,4-tetrahydro-⊖-carboline-2-carbodithioate:

In the same manner as described in Example 39 by using (1RS, 3RS)-cis-1-propyl-3-hydroxymethyl-1,2,3,4-tetrahydro-β-carboline (1.0 g), triethylamine (0.83 g), $CS_2$ (0.62 g), methyl iodide (1.16 g) and dimethylsulfoxide (15 ml), there is prepared the title compound (1.1 g, 80%) as white powder, NMR ($CDCl_3$, δ): 2.72 (s, 3H, $CSSCH_3$); Mass m/e: 334 (M+), 286 (M+—$CH_3SH$).

EXAMPLE 41

Methyl (1RS, 3SR)-trans-1-propyl-3-hydroxymethyl-1,2,3,4-tetrahydro-β-carboline-2-carbodithioate:

In the same manner as described in Example 39 by using (1RS, 3SR)-trans-1-propyl-3-hydroxymethyl-1,2,3,4-tetrahydro-β-carboline (1.18 g), triethylamine (0.98 g), $CS_2$ (0.74 g), methyl iodide (1.37 g) and dimethylsulfoxide (23 ml), there is prepared the title compound (720 mg, 44%) as white powder, NMR ($CDCl_3$, δ): 2.70 (s, 3H, $CSSCH_3$); Mass m/e: 334 (M+), 286 (M+—$CH_3SH$).

EXAMPLE 42

Methyl (3R)-3-(2-hydroxyethyl)-1,2,3,4-tetrahydro-β-carboline-2-carbodithioate:

(3R)-3-(2-Hydroxyethyl)-1,2,3,4-tetrahydro-β-carboline (94 mg) is dissolved in 80% methanol (2.4 ml), and thereto are added $CS_2$ (0.026 ml) and triethylamine (0.061 ml). The mixture is stirred at room temperature for 30 minutes, and thereto is added dropwise methyl iodide (0.027 ml), and the mixture is stirred at room temperature for 4 hours. The reaction mixture is distilled to remove the solvent. The residue is dissolved in ethyl acetate. The solution is washed with water, dried over sodium sulfate and then distilled to remove the solvent. The residue is purified by thin layer chromatography (solvent, ethyl acetate:n-hexane=2:3) to give the title compound (51 mg, 38.3%) as colorless needles, m.p. 166°–167° C., NMR ($CDCl_3$, δ): 2.72 (s, 3H, $CSSCH_3$); Mass m/e: 306 (M+), 258 (M+—$CH_3SH$); $[α]_D^{20}$ −178.0° (c=0.1, methanol).

EXAMPLE 43

4-Aminobenzyl (3S)-3-hydroxymethyl-1,2,3,4-tetrahydro-β-carboline-2-carbodithioate:

4-N-Formylaminobenzyl (3S)-3-hydroxymethyl-1,2,3,4-tetrahydro-β-carboline-2-carbodithioate (412 mg) is dissolved in dimethylformamide (10 ml), and thereto is added 6N HCl (10 ml), and the mixture is stirred at room temperature overnight. The reaction mixture is diluted with water and is adjusted to pH 10 with 10N NaOH. The precipitates are collected by filtration, washed with water and then dried to give the title compound (192 mg, 50%) as pale yellow powder, NMR (DMSO-$d_6$, δ): 4.40 (s, 2H,

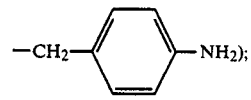

Mass m/e: 244 (M+—

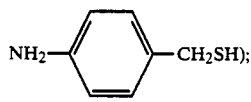

$[α]_D^{20}$ +123.6° (c=0.5, dimethylformamide).

REFERENCE EXAMPLE 1

(1) Methyl (3S)-1,2,3,4-tetrahydro-β-carboline-3-carboxylate:

L-Tryptophan methyl ester hydrochloride (5.09 g) is dissolved in methanol (60 ml) and thereto is added 35% formaldehyde (1.89 g), and the mixture is stirred at room temperature overnight. After distilling off the solvent, the resulting residue is recrystallized from methanol to give the title compound in the form of hydrochloride (4.42 g, 82.9%) as colorless needles, m.p. 250°–253° C.

The hydrochloride obtained above is dissolved in water and is treated with aqueous ammonia to give the corresponding free base, m.p. 168°–170° C., $[α]_D^{20}$ −64.3° (c=1.1, methanol).

(2) (3S)-3-Hydroxymethyl-1,2,3,4-tetrahydro-β-carboline:

A mixture of methyl (3S)-1,2,3,4-tetrahydro-β-carboline-3-carboxylate (15 g), $NaBH_4$ (6.99 g), and 80% ethanol (225 ml) is stirred at room temperature for 12 hours, and then refluxed for 1.5 hour. The insoluble materials are filtered and washed with hot ethanol. The filtrate and the washing are combined and distilled to remove the solvent. Water (40 ml) is added to the residue, and the solution is stirred for 40 minutes. The precipitates are collected by filtration, dried and then recrystallized from ethanol to give the title compound (9.03 g, 79.4%) as colorless needles, m.p. 191°–193° C., $[α]_D^{20}$ −84.6° (c=1.0, methanol).

In the same manner as described in the above (1) and (2) by using D-tryptophan or DL-tryptophan, there are prepared the following compounds.

(3R)-3-Hydroxymethyl-1,2,3,4-tetrahydro-β-carboline;
colorless needles, m.p. 192°–194° C.

$[\alpha]_D^{20} +82.9°$ (c=1.0, methanol)
(3RS)-3-Hydroxymethyl-1,2,3,4-tetrahydro-β-carboline;
colorless needles, m.p. 187°–188° C.

REFERENCE EXAMPLE 2

(1) Methyl (1RS, 3RS)-cis-1-butyl-1,2,3,4-tetrahydro-β-carboline-3-carboxylate and methyl (1RS, 3SR)-trans-1-butyl-1,2,3,4-tetrahydro-β-carboline-3-carboxylate:

A mixture of DL-tryptophan methyl ester hydrochloride (30.49 g), n-valeraldehyde (12.4 g) and methanol (400 ml) is refluxed for 48 hours and then concentrated to about 1/5 volume. After cooling, the precipitates are separated by filtration and recrystallized from methanol to give methyl (1RS, 3RS)-cis-1-butyl-1,2,3,4-tetrahydro-β-carboline-3-carboxylate hydrochloride (20.5 g, 53%), m.p. 218° C. (decomp.) The hydrochloride thus obtained is treated with aqueous ammonia and recrystallized from diisopropyl ether-isopropanol to give the corresponding free base, m.p. 85°–87° C.

The filtrate obtained after filtration of precipitates is concentrated, and to the residue is added water. The aqueous solution is made alkaline with aqueous ammonia and then extracted with chloroform. The extract is washed with water, dried over sodium sulfate and distilled to remove the solvent. The residue is purified by silica gel column chromatography (solvent: chloroform-methanol=500:1) and then recrystallized from isopropyl ether-n-hexane to give methyl (1RS, 3SR)-trans-1-butyl-1,2,3,4-tetrahydro-β-carboline-3-carboxylate (8.6 g, 25%), m.p. 102°–103° C.

(2) (1RS,3RS)-cis-1-Butyl-3-hydroxymethyl-1,2,3,4-tetrahydro-β-carboline:

A mixture of methyl (1RS, 3RS)-cis-1-butyl-1,2,3,4-tetrahydro-β-carboline-3-carboxylate (1.5 g), NaBH$_4$ (0.53 g), ethanol (25 ml) and water (1 ml) is stirred at room temperature for 20 hours, and then distilled to remove the solvent. Methanol is added to the residue, and the mixture is stirred for 30 minutes and then distilled to remove the solvent. To the residue is added water, and the mixture is extracted with chloroform. The extract is washed with water, dried over sodium sulfate and distilled to remove the solvent. The residue is recrystallized from ethanol-methanol to give the title compound (1.15 g, 86%), as colorless needles, m.p. 222°–223° C.

(3) (1RS, 3SR)-trans-1-Butyl-3-hydroxymethyl-1,2,3,4-tetrahydro-β-carboline:

A mixture of methyl (1RS, 3SR)-trans-1-butyl-1,2,3,4-tetrahydro-β-carboline-3-carboxylate (2.5 g), NaBH$_4$ (0.9 g), ethanol (34 ml) and water (1 ml) is treated in the same manner as described in the above (2) to give the title compound, which is recrystallized from ethanol. Yield, 1.80 g (80%), colorless prisms, m.p. 175°–176° C.

REFERENCE EXAMPLE 3

(1) Methyl (1RS, 3SR)-trans-2-benzyl-1-methyl-1,2,3,4-tetrahydro-β-carboline-3-carboxylate and methyl (1RS,3RS)-cis-2-benzyl-1-methyl-1,2,3,4-tetrahydro-β-carboline-3-carboxylate:

N$^b$-Benzyl-DL-tryptophan methyl ester (34.48 g) is dissolved in methanol (340 ml) and thereto is added acetaldehyde (5.23 g), and the mixture is heated at 50° C. for 5 hours. To the mixture is further added acetaldehyde (10.5 g), and the mixture is heated at 50° C. overnight and then distilled to remove the solvent. To the residue is added water, and the mixture is made alkaline with conc.NH$_4$OH and extracted with ethyl acetate. The extract is washed with water, dried over sodium sulfate and distilled to remove the solvent. The residue is purified by silica gel column chromatography (solvent: chloroform) to give methyl (1RS, 3SR)-trans-2-benzyl-1-methyl-1,2,3,4-tetrahydro-β-carboline-3-carboxylate, which is recrystallized from methanol, yield: 16.1 g (48%), colorless needles, m.p. 143°–144° C.; and further methyl (1RS, 3RS)-cis-2-benzyl-1-methyl-1,2,3,4-tetrahydro-β-carboline-3-carboxylate, 3.15 g (9%), as powders.

(2) Methyl (1RS, 3SR)-trans-1-methyl-1,2,3,4-tetrahydro-β-carboline-3-carboxylate;

Methyl (1RS, 3SR)-trans-2-benzyl-1-methyl-1,2,3,4-tetrahydro-β-carboline-3-carboxylate (14.0 g) is dissolved in methanol (600 ml), and thereto is added 10% Pd-C (1.0 g). The mixture is subjected to catalytic reduction under atmospheric pressure. After the reaction, the catalyst is removed by filtration and washed with methanol. The filtrate and the washing liquid are combined and distilled to remove the solvent. The residue is recrystallized from methanol-isopropyl ether to give the title compound (10.08 g, 98.5%) as colorless prisms, m.p. 152°–154° C.

(3) (1RS, 3SR)-trans-3-Hydroxymethyl-1-methyl-1,2,3,4-tetrahydro-β-carboline:

LiAlH$_4$ (1.0 g) is suspended in absolute tetrahydrofuran (40 ml) and thereto is added dropwise a solution of methyl (1RS, 3SR)-trans-1-methyl-1,2,3,4-tetrahydro-β-carboline-3-carboxylate (4.15 g) in absolute tetrahydrofuran (40 ml) at 0° to 5° C., and the mixture is stirred at the same temperature for 1.5 hour. To the reaction mixture hydrous tetrahydrofuran is added and said mixture is filtered. The residue is washed with tetrahydrofuran. The filtrate and the washing liquid are combined and then concentrated. The residue is recrystallized from isopropyl alcohol-methanol to give the title compound (2.98 g, 81%) as colorless prisms, m.p. 197°–198° C.

REFERENCE EXAMPLE 4

(1) Methyl (1S, 3S)-1-methyl-1,2,3,4-tetrahydro-β-carboline-3-carboxylate hydrochloride:

(1S, 3S)-1-Methyl-1,2,3,4-tetrahydro-β-carboline-3-carboxylic acid (63.4 g) is suspended in methanol (700 ml) and thereto is added dropwise SOCl$_2$ (39.3 g) under ice cooling. The mixture is stirred at room temperature for 19 hours and thereafter refluxed for 4 hours. The reaction mixture is distilled to remove the solvent, and the residue is recrystallized from methanol to give the title compound (68.1 g, 88%) as colorless needles, m.p. 251°–253° C., $[\alpha]_D^{20} -89.4°$ (c=1.0, methanol).

(2) (1S, 3S)-3-Hydroxymethyl-1-methyl-1,2,3,4-tetrahydro-β-carboline:

Methyl (1S, 3S)-1-methyl-1,2,3,4-tetrahydro-β-carboline-3-carboxylate hydrochloride (66.3 g) is dissolved in a mixture of ethanol (900 ml) and water (100 ml), and thereto is added NaBH$_4$ (35.8 g) over a period of 20 minutes. The mixture is stirred at room temperature for 18 hours, and to the reaction mixture is added methanol (500 ml), and the mixture is stirred for 2 hours. After filtering off the undissolved materials, the filtrate is concentrated. The residue is extracted with chloroform, and the extract is dried over sodium sulfate and distilled to remove the solvent. The residue is recrystallized from methanol to give the title compound (30.5 g, 60%) as colorless needles, m.p. 197°–198° C., $[\alpha]_D^{20} -73.0°$ (c=1.0, methanol).

In the same manner as described in the above (1) and (2) by using (1R, 3R)- and (1RS, 3RS)-cis-1-methyl-1,2,3,4-tetrahydro-β-carboline-3-carboxylic acid, there are prepared the following compounds.

(1R, 3R)-3-Hydroxymethyl-1-methyl-1,2,3,4-tetrahydro-β-carboline;
colorless needles, m.p. 198°–200° C.
$[\alpha]_D^{20}$ +72.4° (c=1.0, methanol)
(1RS, 3RS)-cis-3-Hydroxymethyl-1-methyl-1,2,3,4-tetrahydro-β-carboline;
colorless needles, m.p. 176°–178° C.

REFERENCE EXAMPLE 5

(1) (1RS, 3RS)-cis-1-Ethyl-3-hydroxymethyl-1,2,3,4-tetrahydro-β-carboline:

LiAlH$_4$ (500 mg) is suspended in absolute tetrahydrofuran (30 ml) and thereto is added dropwise a solution of methyl (1RS, 3RS)-cis-1-ethyl-1,2,3,4-tetrahydro-β-carboline-3-carboxylate (2.45 g) in absolute tetrahydrofuran (30 ml) at 5°–10° C. The mixture is stirred at room temperature for 1 hour, and thereto is added aqueous tetrahydrofuran. The mixture is filtered, and the residue is washed with tetrahydrofuran. The filtrate and the washing liquid are combined, dried over sodium sulfate, and distilled to remove the solvent. The residue is recrystallized from methanol to give the title compound (1.84 g, 84.4%), as colorless needles, m.p. 205°–206° C.

(2) (1RS, 3SR)-trans-1-Ethyl-3-hydroxymethyl-1,2,3,4-tetrahydro-β-carboline:

In the same manner as described in the above (1) by using methyl (1RS, 3SR)-trans-1-ethyl-1,2,3,4-tetrahydro-β-carboline-3-carboxylate (3.58 g), LiAlH$_4$ (500 mg) and absolute tetrahydrofuran (60 ml), there is prepared the title compound (1.96 g, 85.2%) as colorless prisms, m.p. 170.5°–171.0° C. (recrystallized from methanol).

REFERENCE EXAMPLE 6

(1) (1RS, 3RS)-cis-1,3-Dihydroxymethyl-1,2,3,4-tetrahydro-β-carboline:

Methyl (1RS, 3RS)-cis-1-hydroxymethyl-1,2,3,4-tetrahydro-β-carboline-3-carboxylate (1.3 g) is dissolved in a mixture of ethanol (60 ml) and water (25 ml), and thereto is added NaBH$_4$ (0.76 g). The mixture is stirred at room temperature for 20 hours, and then distilled to remove the solvent. The residue is dissolved in hot ethanol, and the undissolved materials are filtered off. The filtrate is evaporated to remove the solvent to give the title compound (730 mg, 63%) as white powder, Mass m/e: 232 (M+), 214 (M+-H$_2$O).

(2) (1RS, 3SR)-trans-1,3-Dihydroxymethyl-1,2,3,4-tetrahydro-β-carboline:

In the same manner as described in the above (1) by using methyl (1RS, 3SR)-trans-1-hydroxymethyl-1,2,3,4-tetrahydro-β-carboline-3-carboxylate (1.3 g), 80% ethanol (50 ml) and NaBH$_4$ (0.76 g), there is prepared the title compound (870 mg, 75%), as white powder, Mass m/e: 232 (M+), 214 (M+-H$_2$O).

REFERENCE EXAMPLE 7

(1) (3R)-2-Benzyloxycarbonyl-3-methoxycarbonylmethyl-1,2,3,4-tetrahydro-β-carboline:

To a solution of (3R)-2-benzyloxycarbonyl-1,2,3,4-tetrahydro-β-carboline-3-carboxylic acid (1.05 g) (Chem. Pharm. Bull. 25 (1977), 1559) in absolute tetrahydrofuran (50 ml) are added N-methylmorpholine (0.3 g) and isobutyl chloroformate (0.39 ml) at −5° C. The mixture is stirred at −5° C. for 40 minutes, and thereto is added dropwise a solution of diazomethane in ether (prepared from N-methylnitrosourea (1.55 g) and 40% KOH (4.5 ml)). The mixture is stirred at −5° C. for 4.5 hours and then distilled to remove the solvent. The residue is dissolved in methanol (40 ml), and thereto is added dropwise a solution of silver benzoate (90 mg) in triethylamine (0.9 ml). The mixture is stirred for 1 hour and filtered. The filtrate is distilled to remove the solvent. The residue is dissolved in ethyl acetate, and the mixture is washed with 10% hydrochloric acid, water, saturated aqueous sodium bicarbonate, and water in order, and then dried over magnesium sulfate and distilled to remove the solvent. The residue is purified with silica gel column chromatography to give the title compound (345 mg, 30%), m.p. 173°–174° C., Mass m/e: 378 (M+).

(2) (3R)-2-Benzyloxycarbonyl-3-(2-hydroxyethyl)-1,2,3,4-tetrahydro-β-carboline:

(3R)-2-Benzyloxycarbonyl-3-methoxycarbonylmethyl-1,2,3,4-tetrahydro-β-carboline (580 mg) is dissolved in a mixture of ethanol (6 ml)-tetrahydrofuran (12 ml)-water (4.5 ml). To the mixture is added dropwise a solution of NaBH$_4$ (347 mg) in 80% ethanol (5 ml) under ice-cooling. The mixture is stirred at room temperature for 16 hours. The reaction mixture is treated in a conventional manner to give the title compound (481 mg, 90%) as colorless needles, m.p. 125°–127° C. (recrystallized from ethyl acetate-n-hexane).

(3) (3R)-3-(2-Hydroxyethyl)-1,2,3,4-tetrahydro-β-carboline:

(3R)-2-Benzyloxycarbonyl-3-(2-hydroxyethyl)-1,2,3,4-tetrahydro-β-carboline (440 mg) is dissolved in ethanol (10 ml), and thereto is added 10% Pd-C (200 mg), and the mixture is subjected to catalytic reduction in hydrogen gas under atmospheric pressure, and the reaction mixture is treated in a conventional manner to give the title compound (205 mg, 75%) as white powder, Mass m/e: 216 (M+).

REFERENCE EXAMPLE 8

(1) Methyl (1RS, 3RS)-cis-1-n-propyl-1,2,3,4-tetrahydro-β-carboline-3-carboxylate and methyl (1RS, 3SR)-trans-1-n-propyl-1,2,3,4-tetrahydro-β-carboline-3-carboxylate:

A mixture of DL-tryptophan methyl ester hydrochloride (33 g), n-butyraldehyde (21.0 g) and methanol (450 ml) is refluxed for 48 hours. After the reaction, the reaction mixture is concentrated to about ⅓ in volume and allowed to stand. The precipitated crystals are collected by filtration and recrystallized from methanol to give methyl (1RS, 3RS)-cis-1-n-propyl-1,2,3,4-tetrahydro-β-carboline-3-carboxylate hydrochloride (15.4 g, 38.4%) as colorless prisms, m.p. 205°–207° C.

The mother liquor obtained in the above procedure is concentrated, and the residue is dissolved in water, and the solution is made alkaline with aqueous ammonia and extracted with chloroform. The chloroform layer is washed with water, dried, and then distilled to remove the solvent. The residue is purified by silica gel column chromatography (solvent, CHCl$_3$: methanol=300:1 by volume) to give the following compounds:

Methyl (1RS, 3RS)-cis-1-n-propyl-1,2,3,4-tetrahydro-β-carboline-3-carboxylate (2.5 g, 7%), colorless needles, m.p. 98°–100° C. (recrystallized from isopropyl ether—isopropanol).

Methyl (1RS, 3SR)-trans-1-n-propyl-1,2,3,4-tetrahydro-β-carboline-3-carboxylate (8.2 g, 23%), colorless prisms, m.p. 116°–118° C. (recrystallized from isopropyl ether).

(2) (1RS, 3RS)-cis-3-Hydroxymethyl-1-n-propyl-1,2,3,4-tetrahydro-β-carboline:

A mixture of methyl (1RS, 3RS)-cis-1-n-propyl-1,2,3,4-tetrahydro-β-carboline-3-carboxylate (3.4 g), NaBH₄ (1.2 g) and 90% ethanol (40 ml) is stirred at room temperature for 20 hours, and inorganic substances are removed off by filtration. The filtrate is concentrated, and to the residue is added a small amount of water. The mixture is extracted with chloroform, and the extract is washed with water, dried over sodium sulfate, and then distilled to remove the solvent. The residue is recrystallized from aqueous methanol to give the title compound (2.3 l g, 75%), colorless needles, m.p. 218°–219° C.

(3) (1RS, 3SR)-trans-3-Hydroxymethyl-1-n-propyl-1,2,3,4-tetrahydro-carboline:

A mixture of methyl (1RS, 3SR)-trans-1-n-propyl-1,2,3,4-tetrahydro-β-carboline-3-carboxylate (2.0 g), NaBH₄ (0.73 g) and 90% ethanol (31 ml) is reacted in the same manner as described in the above (2) to give the title compound (1.18 g, 64%), colorless needles, m.p. 170.5°–171° C. (recrystallized from aqueous methanol).

What is claimed is:

1. A tetrahydro-β-carboline derivative of

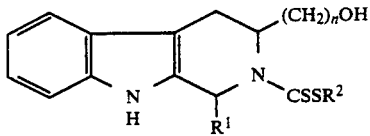

(I)

wherein R¹ is hydrogen atom, a lower alkyl group, a cycloalkyl group, phenyl group or a hydroxy-substituted lower alkyl group, R² is hydrogen atom, an alkyl group or a group of the formula: —(CH₂)ₘY, Y is thienyl group or an unsubstituted phenyl group or a substituted phenyl group substituted by a substituent selected from the group consisting of a halogen atom, formylamino, amino, nitro, a lower alkyl group having 1 to 4 carbon atoms and a lower alkoxy group having 1 to 4 carbon atoms and each one of m and n is an integer of 1 or 2 or a pharmaceutically acceptable salt thereof.

2. The compound of claim 1, wherein Y is thienyl group, phenyl group or a phenyl group having a substituent selected from the group consisting of a halogen atom, formylamino, amino, nitro, lower alkyl and lower alkoxy.

3. A pharmaceutically acceptable salt of the compound of claim 2, wherein R² is hydrogen atom or a group: —(CH₂)ₘY and Y is amino-phenyl.

4. The compound of claim 2, wherein R¹ is hydrogen atom, methyl, ethyl, propyl, butyl, hydroxymethyl, cyclohexyl or phenyl, and R² is hydrogen atom, methyl, ethyl, propyl, butyl, hexyl, decyl, benzyl, 2-thenyl, phenylethyl, 4-chlorobenzyl, 4-(N-formylamino)benzyl, 4-amonobenzyl, 4-nitrobenzyl, 4-methylbenzyl or 4-methoxybenzyl.

5. A pharmaceutically acceptable salt of the compound of claim 4, wherein R² is hydrogen atom or 4-aminobenzyl.

6. The compound of claim 4, wherein R¹ is hydrogen atom, methyl, ethyl or hydroxymethyl; R² is hydrogen atom, methyl, ethyl, propyl, butyl, benzyl, 4-chlorobenzyl, 2-thenyl or 4-methoxybenzyl; and n is an integer of 1.

7. A pharmaceutically acceptable salt of the compound of claim 6, wherein R² is hydrogen atom.

8. The compound of claim 6, wherein R¹ is hydrogen atom or methyl.

9. A pharmaceutically acceptable salt of the compound of claim 8, wherein R² is hydrogen atom.

10. The compound of claim 8, wherein R² is hydrogen atom, methyl or ethyl.

11. A pharmaceutically acceptable salt of the compound of claim 10, wherein R² is hydrogen atom.

12. The compound of claim 4, wherein R¹ is hydrogen atom, R² is methyl or 4-chlorobenzyl and n is an integer of 2.

13. The compound of claim 10, which is (3S)-3-hydroxymethyl-1,2,3,4-tetrahydro-β-carboline-2-carbodithioic acid or a pharmaceutically acceptable salt thereof.

14. The compound of claim 10, which is methyl (3S)-3-hydroxymethyl-1,2,3,4-tetrahydro-β-carboline-2-carbodithioate.

15. The compound of claim 10, which is methyl (3R) or (3RS)-3-hydroxymethyl-1,2,3,4-tetrahydro-β-carboline-2-carbodithioate.

16. The compound of claim 10, which is methyl (1S, 3S), (1R, 3R) or (1RS, 3RS)-3-hydroxymethyl-1-methyl-1,2,3,4-tetrahydro-β-carboline-2-carbodithioate.

17. The compound of claim 12, which is methyl (3R)-3-(2-hydroxyethyl)-1,2,3,4-tetrahydro-β-carboline-2-carbodithioate.

18. A composition for treating or preventing liver damage, wherein the liver damage is a liver disease associated with centrilobular necrosis, periportal necrosis, discrete lobular necrosis, mesenchymal reaction, fatty liver, drug-induced hepatopathy, viral hepatitis, alcoholic hepatitis, jaundice or hepatocirrhosis, which comprises as the essential active ingredient a therapeutically or prophylactically effective amount of a tetrahydro-β-carboline derivative as claimed in claim 1 in admixture with a pharmaceutically acceptable carrier or diluent.

19. A composition for treating or preventing liver damage, wherein the liver damage is a liver disease associated with centrilobular necrosis, periportal necrosis, discrete lobular necrosis, mesenchymal reaction, fatty liver, drug-induced hepatopathy, viral hepatitis, alcoholic hepatitis, jaundice or hepatocirrhosis, which comprises as the essential active ingredient a therapeutically or prophylactically effective amount of a tetrahydro-β-carboline derivative as claimed in claim 2 in admixture with a pharmaceutically acceptable carrier or diluent.

20. A composition for treating or preventing liver damage, wherein the liver damage is a liver disease associated with centrilobular necrosis, periportal necrosis, discrete lobular necrosis, mesenchymal reaction, fatty liver, drug-induced hepatopathy, viral hepatitis, alcoholic hepatitis, jaundice or hepatocirrhosis, which comprises as the essentail active ingredient a therapeutically or prophylactically effective amount of a tetrahydro-β-carboline derivative as claimed in claim 3 in admixture with a pharmaceutically acceptable carrier or diluent.

21. A composition for treating or preventing liver damage, wherein the liver damage is a liver disease associated with centrilobular necrosis, periportal necrosis, discrete lobular necrosis, mesenchymal reaction, fatty liver, drug-induced hepatopathy, viral hepatitis, alcoholic hepatitis, jaundice or hepatocirrhosis, which comprises as the essential active ingredient a therapeutically or prophylactically effective amount of a tetrahydro-β-carboline derivative as claimed in claim 4 in admixture with a pharmaceutically acceptable carrier or diluent.

22. A composition for treating or preventing liver damage, wherein the liver damage is a liver disease associated with centrilobular necrosis, periportal necrosis, discrete lobular necrosis, mesenchymal reaction, fatty liver, drug-induced hepatopathy, viral hepatitis, alcoholic hepatitis, jaundice or hepatocirrhosis, which comprises as the essential active ingredient a therapeutically or prophylactically effective amount of a tetrahydro-β-carboline derivative as claimed in claim 6 in admixture with a pharmaceutically acceptable carrier or diluent.

23. A composition for treating or preventing liver damage, wherein the liver damage is a liver disease associated with centrilobular necrosis, periportal necrosis, discrete lobular necrosis, mesenchymal reaction, fatty liver, drug-induced hepatopathy, viral hepatitis, alcoholic hepatitis, jaundice or hepatocirrhosis, which comprises as the essential active ingredient a therapeutically or prophylactically effective amount of a tetrahydro-β-carboline derivative as claimed in claim 10 in admixture with a pharmaceutically acceptable carrier or diluent.

24. A composition for treating or preventing liver damage, wherein the liver damage is a liver disease associated with centrilobular necrosis, periportal necrosis, discrete lobular necrosis, mesenchymal reaction, fatty liver, drug-induced hepatopathy, viral hepatitis, alcoholic hepatitis, jaundice or hepatocirrhosis, which comprises as the essential active ingredient a therapeutically or prophylactically effective amount of a tetrahydro-β-carboline derivative as claimed in claim 12 in admixture with a pharmaceutically acceptable carrier or diluent.

25. A composition for treating or preventing liver damage, wherein the liver damage is a liver disease associated with centrilobular necrosis, periportal necrosis, discrete lobular necrosis, mesenchymal reaction, fatty liver, drug-induced hepatopathy, viral hepatitis, alcoholic hepatitis, jaundice or hepatocirrhosis, which comprises as the essential active ingredient a therapeutically or prophylactically effective amount of a tetrahydro-β-carboline derivative as claimed in claim 14 in admixture with a pharmaceutically acceptable carrier or diluent.

26. A method for treating or preventing liver damage, wherein the liver damage is a liver disease associated with centrilobular necrosis, periportal necrosis, discrete lobular necrosis, mesenchymal reaction, fatty liver, drug-induced hepatopathy, viral hepatitis, alcoholic hepatitis, jaundice or hepatocirrhosis, which comprises orally or parenterally administering to a patient affected with said liver damage a therapeutically or prophylactically effective amount of a tetrahydro-β-carboline derivative as claimed in claim 1.

27. A method for treating or preventing liver damage, wherein the liver damage is a liver disease associated with centrilobular necrosis, periportal necrosis, discrete lobular necrosis, mesenchymal reaction, fatty liver, drug-induced hepatopathy, viral hepatitis, alcoholic hepatitis, jaundice or hepatocirrhosis, which comprises orally or parenterally administering to a patient affected with said liver damage a therapeutically or prophylactically effective amount of the composition as claimed in claim 18.

28. The method according to claim 26, wherein the dosage rate of the tetrahydro-β-carboline derivative is 0.01 to 250 mg/kg/day.

29. The method according to claim 27, wherein the dosage rate of the tetrahydro-β-carboline derivative is 0.01 to 250 mg/kg/day.

30. The method according to claim 28, wherein the tetrahydro-β-carboline derivative is administered orally at a dosage rate of 0.5 to 50 mg/kg/day.

31. The method according to claim 29, wherein the tetrahydro-β-carboline derivative is administered orally at a dosage rate of 0.5 to 50 mg/kg/day.

32. A method for treating or preventing liver damage, wherein the liver damage is a liver disease associated with centrilobular necrosis, periportal necrosis, discrete lobular necrosis, mesenchymal reaction, fatty liver, drug-induced hepatopathy, viral hepatitis, alcoholic hepatitis, jaundice or hepatocirrhosis, which comprises, orally or parenterally administering to a patient affected with said liver damage, a therapeutically or prophylactically effective amount of tetrahydro-β-carboline derivative as claimed in claim 3.

33. A method for treating or preventing liver damage, wherein the liver damage is a liver disease associated with centrilobular necrosis, periportal necrosis, discrete lobular necrosis, mesenchymal reaction, fatty liver, drug-induced hepatopathy, viral hepatitis, alcoholic hepatitis, jaundice or hepatocirrhosis, which comprises orally or parenterally administering to a patient affected with said liver damage a therapeutically or prophylactically effective amount of the composition as claimed in claim 20.

34. A method for treating or preventing liver damage, wherein the liver damage is a liver disease associated with centrilobular necrosis, periportal necrosis, discrete lobular necrosis, mesenchymal reaction, fatty liver, drug-induced hepatopathy, viral hepatitis, alcoholic hepatitis, jaundice or hepatocirrhosis, which comprises, orally or parenterally administering to a patient affected with said liver damage, a therapeutically or prophylactically effective amount of tetrahydro-β-carboline derivative as claimed in claim 10.

35. A method for treating or preventing liver damage, wherein the liver damage is a liver disease associated with centrilobular necrosis, periportal necrosis, discrete lobular necrosis, mesenchymal reaction, fatty liver, drug-induced hepatopathy, viral hepatitis, alcoholic hepatitis, jaundice or hepatocirrhosis, which comprises orally or parenterally administering to a patient affected with said liver damage a therapeutically or prophylactically effective amount of the composition as claimed in claim 23.

36. A method for treating or preventing liver damage, wherein the liver damage is a liver disease associated with centrilobular necrosis, periportal necrosis, discrete lobular necrosis, mesenchymal reaction, fatty liver, drug-induced hepatopathy, viral hepatitis, alcoholic hepatitis, jaundice or hepatocirrhosis, which comprises, orally or parenterally administering to a patient affected with said liver damage, a therapeutically or prophylactically effective amount of tetrahydro-β-carboline derivative as claimed in claim 14.

37. A method for treating or preventing liver damage, wherein the liver damage is a liver disease associated with centrilobular necrosis, periportal necrosis, discrete lobular necrosis, mesenchymal reaction, fatty liver, drug-induced hepatopathy, viral hepatitis, alcoholic hepatitis, jaundice or hepatocirrhosis, which comprises orally or parenterally administering to a patient affected with said liver damage a therapeutically or prophylactically effective amount of the composition as claimed in claim 25.

* * * * *